United States Patent
Sherman et al.

(10) Patent No.: US 6,664,040 B2
(45) Date of Patent: Dec. 16, 2003

(54) COMPOSITIONS AND METHODS FOR DELIVERY OF A MOLECULE INTO A CELL

(75) Inventors: Michael P. Sherman, San Francisco, CA (US); Warner C. Greene, San Francisco, CA (US); Carlos M.C. de Noronha, San Francisco, CA (US); Ulrich Schubert, Bethesda, MA (US); Peter Henklein, Berlin (GB)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/839,329

(22) Filed: Apr. 20, 2001

(65) Prior Publication Data

US 2002/0022027 A1 Feb. 21, 2002

Related U.S. Application Data

(60) Provisional application No. 60/206,610, filed on May 23, 2000, and provisional application No. 60/267,827, filed on Feb. 9, 2001.

(51) Int. Cl.$^7$ .............................. C12Q 1/70; C12Q 1/02; C12P 1/00; C12N 5/00; C07K 7/00; C07K 1/00; C07K 14/00; C07K 17/00

(52) U.S. Cl. ................................ 435/5; 435/5; 435/29; 435/41; 435/325; 530/350; 530/300; 530/395

(58) Field of Search ............................... 435/5, 29, 41, 435/325; 530/300, 350, 395

(56) References Cited

U.S. PATENT DOCUMENTS 6,001,985 A 12/1999 Kappes et al.

FOREIGN PATENT DOCUMENTS

| WO | WO 94/19456 | | 9/1994 |
|---|---|---|---|
| WO | WO 95/26361 | | 10/1995 |
| WO | WO 96/07741 | | 3/1996 |
| WO | WO 96/08970 A1 | * | 3/1996 |
| WO | WO 98/35032 | | 8/1998 |
| WO | WO 99/09412 | | 2/1999 |
| WO | WO 99/29721 | | 6/1999 |
| WO | WO 00/49038 A3 | | 8/2000 |

OTHER PUBLICATIONS

Geng et al. BioTechiques. 1998; 25 (3): 438, 440, 442 and 444.*
Toy et al. Obstetrics and Gynecology. Jan. 2000; 95 (1): 141–146.*
Fletcher et al. (EMBO Journal. 1997; 16 (16): 5123–5138.*
Cornille et al. Journal of Peptide Research. 1999; 54: 427–435.*
S. Mahalingam et al., "In Vitro and In Vivo Tumor Growth Suppression by HIV–1 Vpr," DNA and Cell Biology, 1997, 16(2): pp. 137–143.
S. Stewart et al., "Lentiviral Delivery of HIV–1 Vpr Protein Induces Apoptosis in Transformed Cells," PNAS, 1999, 96(21): pp. 12039–12043.
B. Zhivotovsky et al., "Tumor Radiosensitivity and Apoptosis," Experimental Cell Research, 1999, 248(1): pp. 10–17.
P. Henklein et al., "Functional and Structural Characterization of Synthetic HIV–1 Vpr That Transduces Cells, Localizes to the Nucleus, and Induces $G_2$ Cell Cycle Arrest," XP–002185470,J. Biol. Chem., 2000, 275(41):32016–32026.
A. Kichler et al., "Efficient DNA Transfection Mediated by the C–Terminal Domain of Human Immunodeficiency Virus Type 1 Viral Protein R," J. Vir., 2000, 74(12):5424–5431.
H. Gras–Masse et al., 1990, "A synthetic protein . . . patients," Int. J. Peptide Res. 36:219–226.
F. Cornille et al., 1999, "Efficient solid–phase . . . studies," Peptide Res. 53:427–435.
M. Nishizawa et al., 1999, "A Carboxy–Terminally . . . Cycle," Virology, 263:313–322.
B.P. Roques et al., 1997, "Structure, biologically . . . NCp7," Biochimie, 79:673–680.
H. de Rocquigny et al., 1997, "The Zinc Fingers . . . Vpr*," The Journal of Biological Chemistry, 272(40):30753–30759.
Y. Jenkins et al., 1998, "Characterization of . . . Pathways," The Journal of Cell Biology, 143(4):875–885.
L.D. Shostak et al., 1999, "Roles of p53 . . . vpr," Experimental Cell Research, 251:156–165.

* cited by examiner

*Primary Examiner*—James Housel
*Assistant Examiner*—Shanon Foley
(74) *Attorney, Agent, or Firm*—Gates & Cooper LLP

(57) ABSTRACT

Provided is a composition comprising a Vpr polypeptide conjugated to a therapeutic molecule. Preferably, the Vpr comprises synthetic Vpr. The therapeutic molecule can comprise any molecule capable of being conjugated to Vpr or a fragment thereof, including a polypeptide, a polynucleotide, and/or a toxin. The invention additionally provides a method for delivering a molecule into a cell. The method comprises contacting the cell with a conjugate comprising a Vpr polypeptide conjugated to the molecule. The invention further provides a method for modulating the expression of a transgene in a cell, a method for killing a target cell population in a subject, a method for increasing the sensitivity of cells to radiation therapy, and a method for inhibiting cell proliferation.

14 Claims, 29 Drawing Sheets

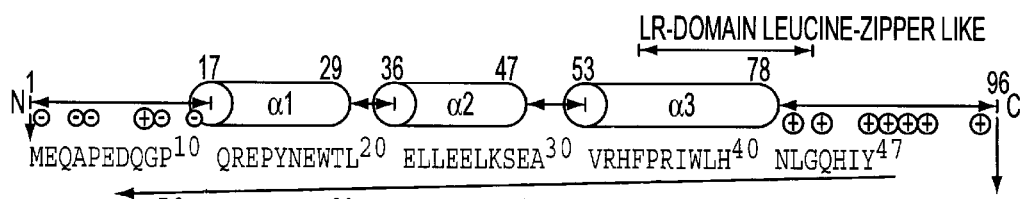
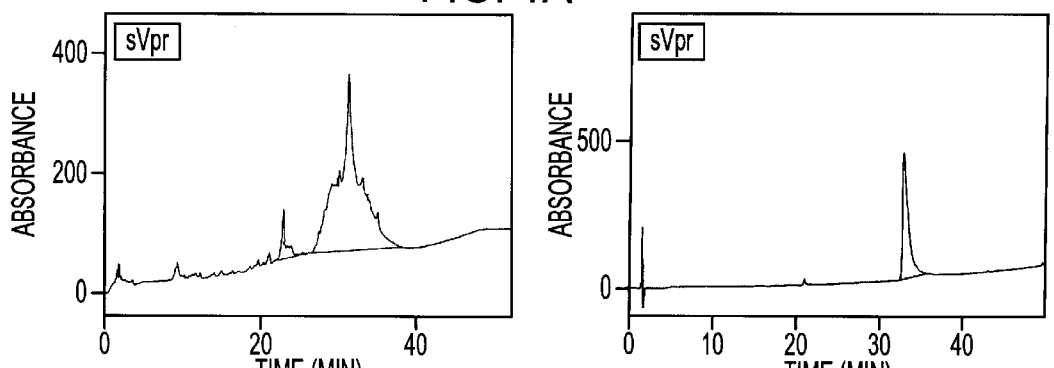
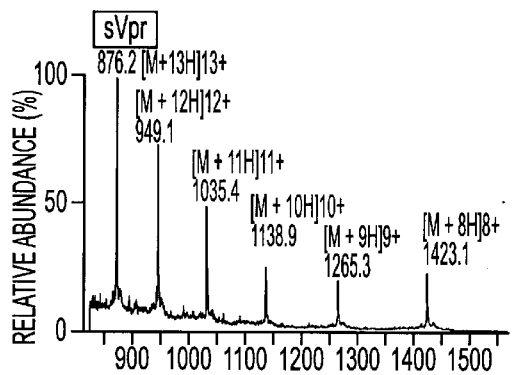
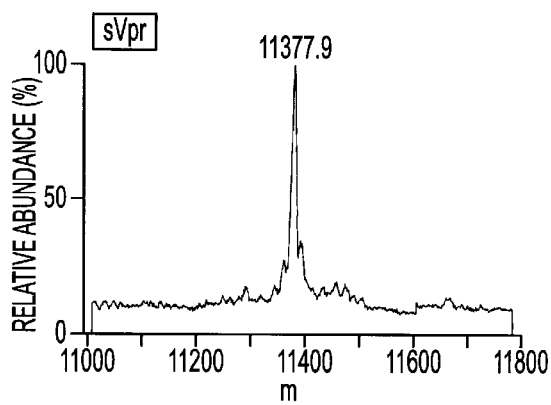
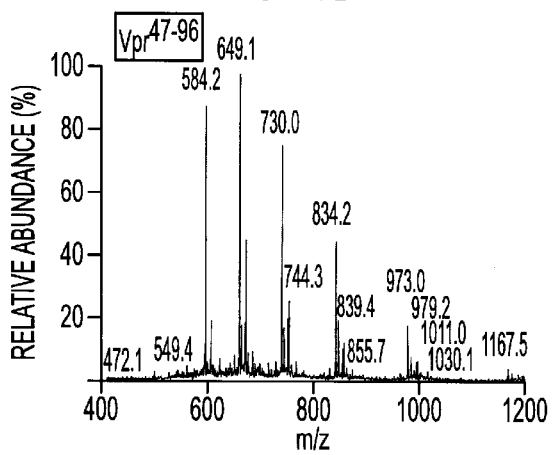
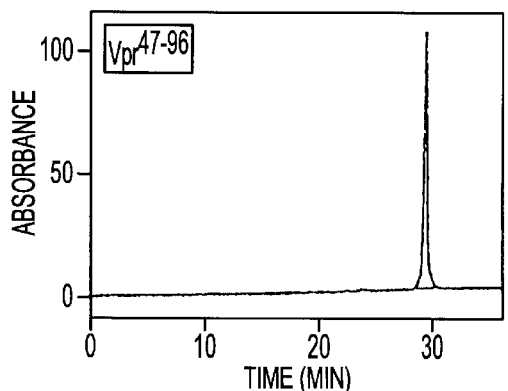

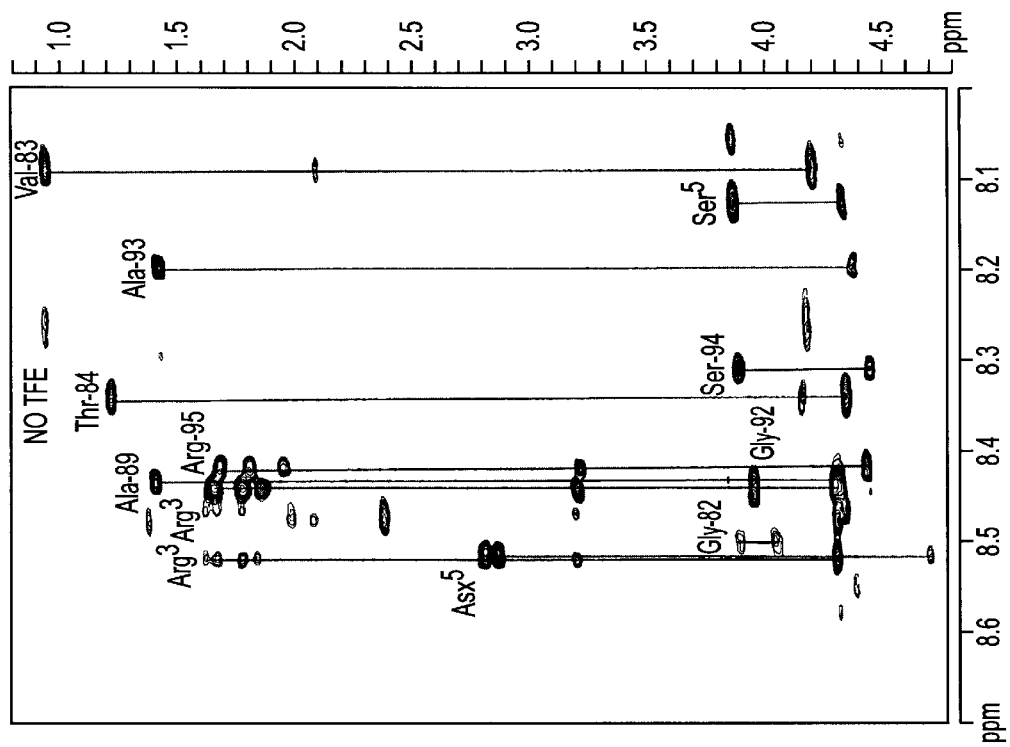
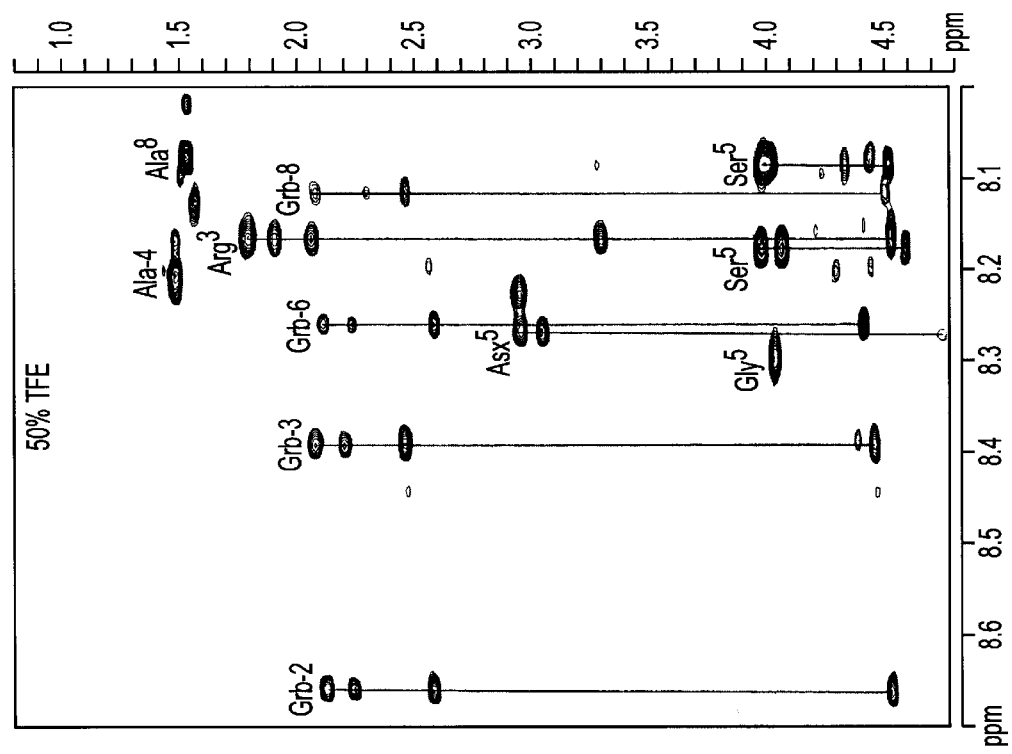

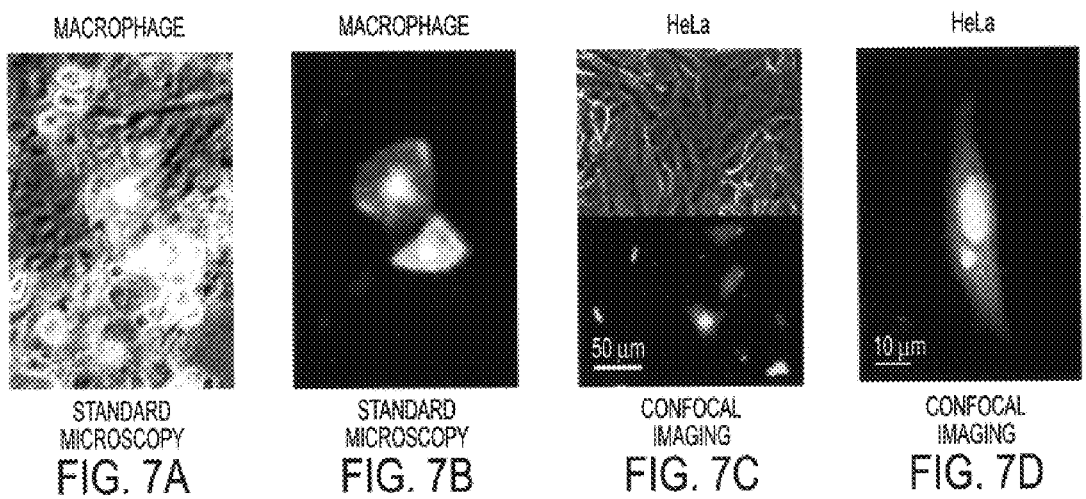

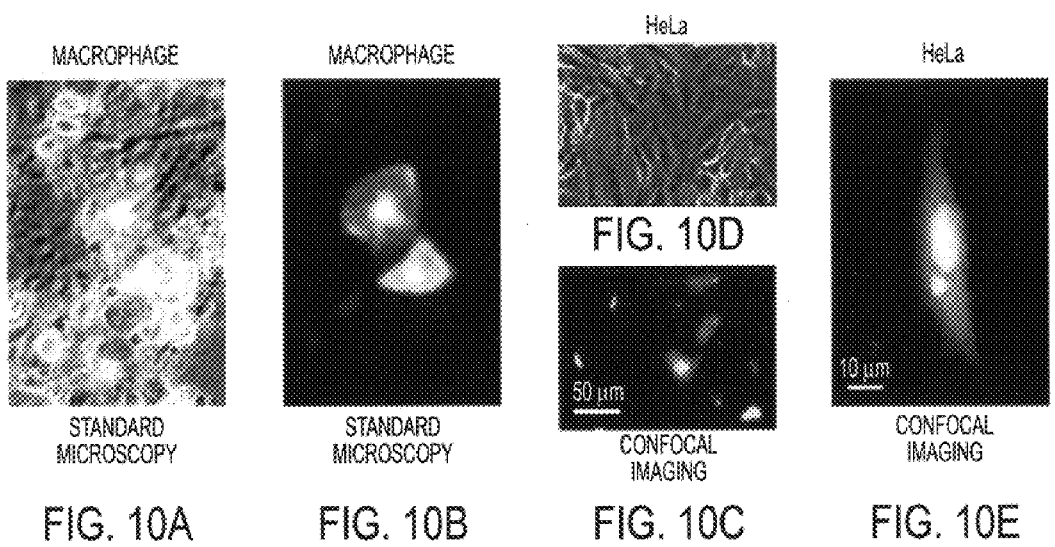

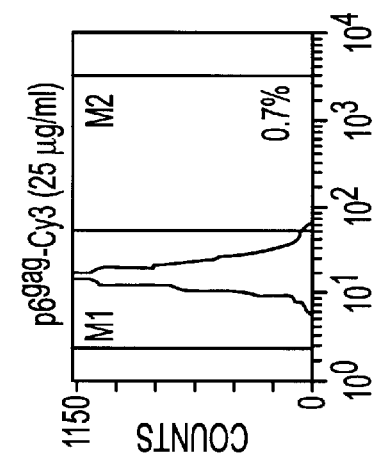
FIG. 12A
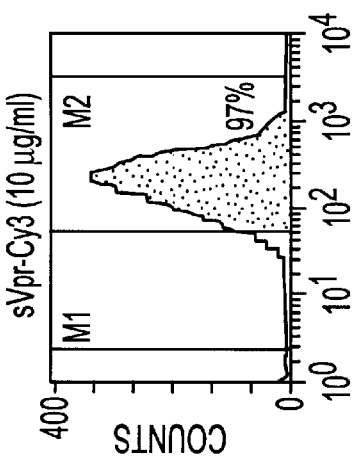
FIG. 12B
FIG. 12C
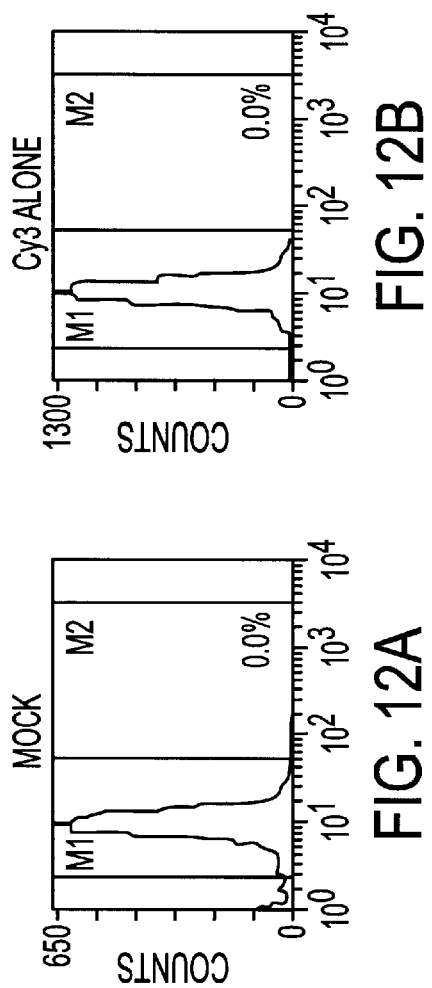
FIG. 12D
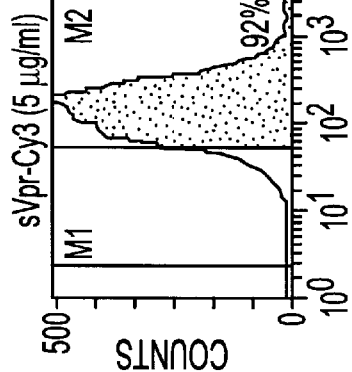
FIG. 12E
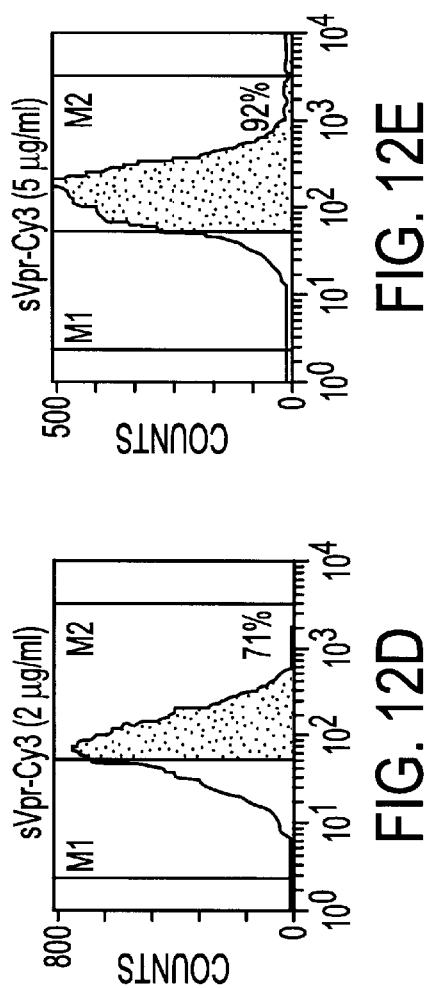
FIG. 12F

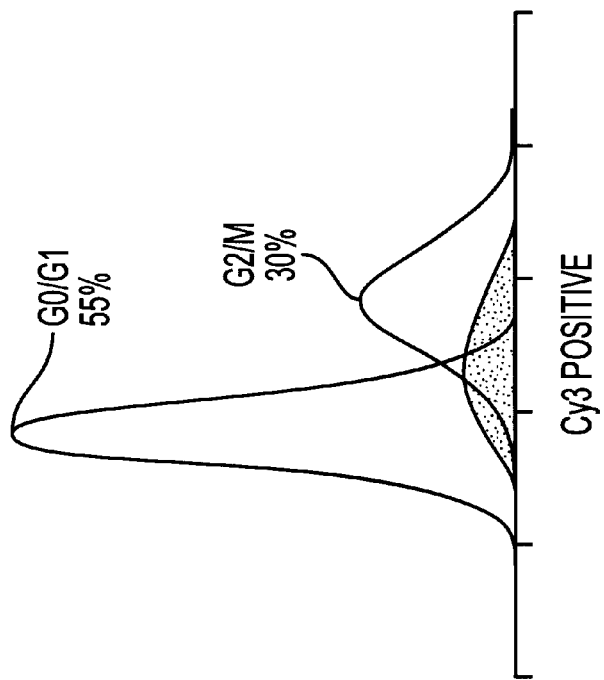
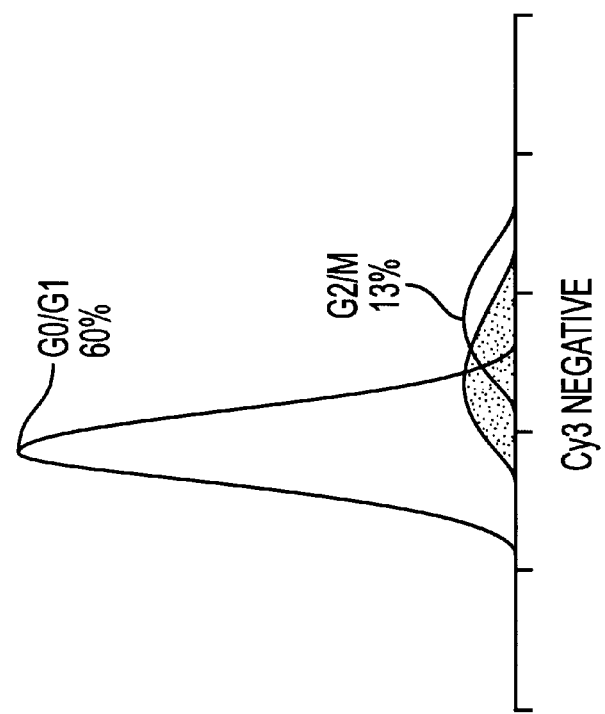

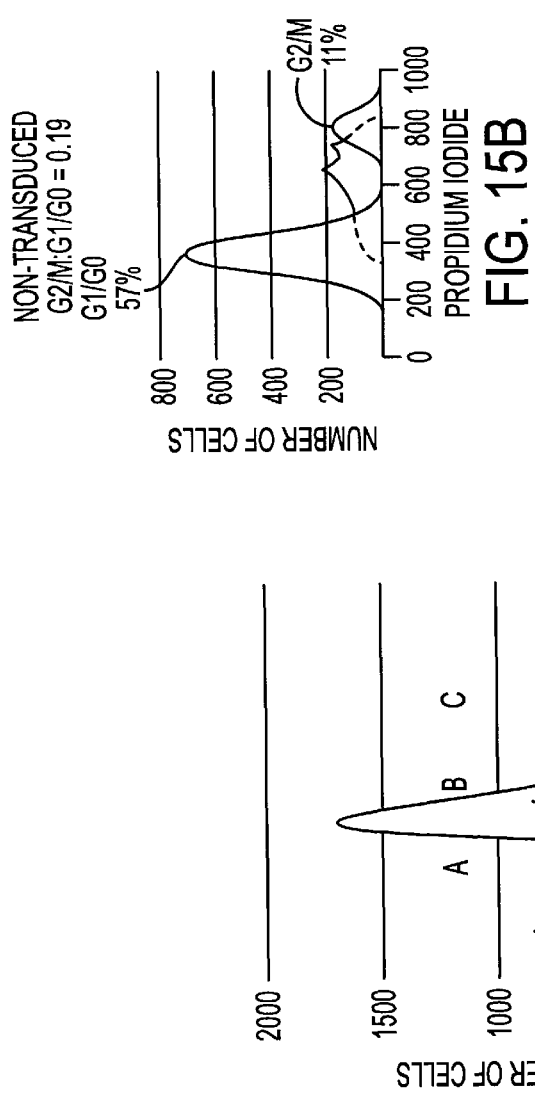
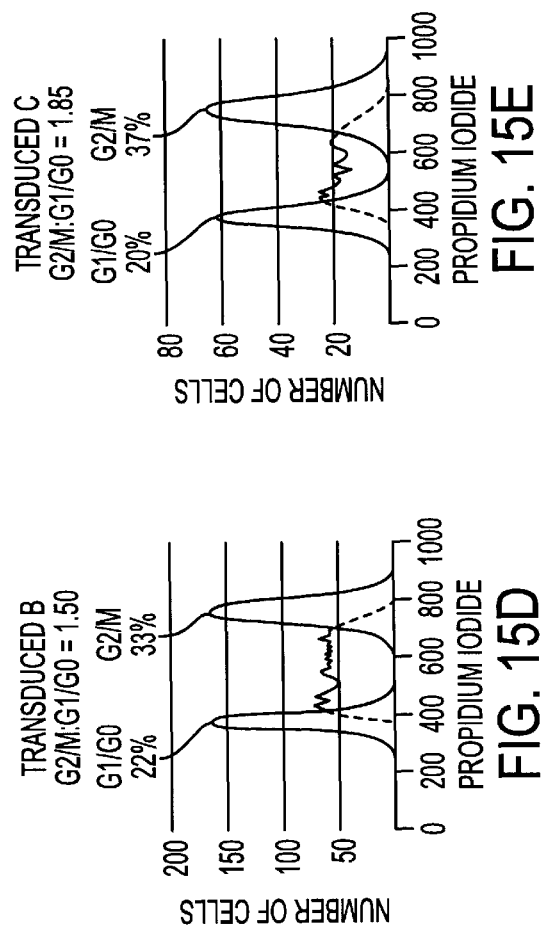
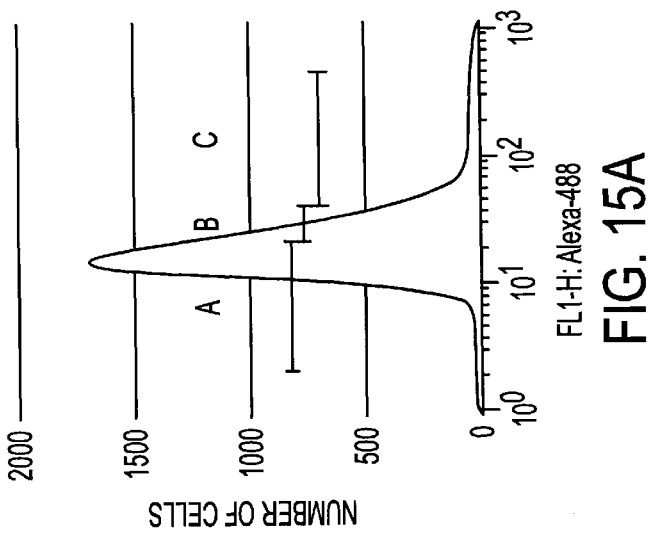

```
          73                          96
NH₂-RIGCRHSRIGVTRQRRARNGASRS-COOH
```

FIG. 21

SEQUENCE LISTING

<160> NUMBER OF SEQ ID NOS: 5

<210> SEQ ID NO 1
<211> LENGTH: 96
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 1

Met Glu Gln Ala Pro Glu Asp Gln Gly Pro Gln Arg Glu Pro Tyr Asn
1               5                   10                  15

Glu Trp Thr Leu Glu Leu Leu Glu Glu Leu Lys Ser Glu Ala Val Arg
            20                  25                  30

His Phe Pro Arg Ile Thr Leu His Asn Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Arg Gln Arg Arg Ala Arg Asn Gly Ala Ser Arg Ser
                85                  90                  95

<210> SEQ ID NO 2
<211> LENGTH: 24
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 2

Arg Ile Gly Cys Arg His Ser Arg Ile Gly Val Thr Arg Gln Arg Arg
1               5                   10                  15

Ala Arg Asn Gly Ala Ser Arg Ser
            20

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide of regulatory virus proteins
      R (vpr) of human immunodeficiency virus type 1 (HIV-1)

<400> SEQUENCE: 3

Arg Ile Gly Cys Arg His Ser Arg Ile Gly Val Thr Arg Gln Arg Arg
1               5                   10                  15

Ala Arg

<210> SEQ ID NO 4
<211> LENGTH: 10
<212> TYPE: PRT
<213> ORGANISM: Artificial Sequence
<220> FEATURE:
<223> OTHER INFORMATION: Human immunodeficiency virus

<400> SEQUENCE: 4

Tyr Gly Lys Lys Arg Arg Gln Arg Arg Arg
1               5                   10

```
<210> SEQ ID NO 5
<211> LENGTH: 6
<212> TYPE: PRT
<213> ORGANISM: Artificial Sequence
<220> FEATURE:
<223> OTHER INFORMATION: Human immunodeficiency virus

<400> SEQUENCE: 5

Arg Gln Arg Arg Ala Arg
 1               5
```

COMPOSITIONS AND METHODS FOR DELIVERY OF A MOLECULE INTO A CELL

This application claims priority of U.S. provisional patent application No. 60/206,610, filed May 23, 2000, and No. 60/267,827, filed Feb. 9, 2001. The entire contents of these applications is incorporated herein by reference.

Throughout this application various publications are referenced. In some instances, the references are indicated by numerals in parentheses, which numerals refer to a list of citations for the corresponding references that appears at the end of the specification. The disclosures of these publications in their entireties are hereby incorporated by reference into this application in order to describe more fully the state of the art to which this invention pertains. This application is related to German patent applications 199 08 752.0 and 199 08 766.0, filed on Feb. 19, 1999 and Feb. 17, 2000, respectively, as well as to the corresponding PCT international patent application filed on Feb. 17, 2000. The disclosures of each of these related patent applications is incorporated herein by reference.

TECHNICAL FIELD OF THE INVENTION

The invention relates to compositions and methods for delivery of a molecule into a cell. More particularly, the invention relates to a Vpr polypeptide or fragment thereof conjugated to a molecule, which conjugate is capable of entering the plasma membrane of a cell. The compositions include pharmaceutical and vaccine compositions, and can be used in a variety of methods, including methods to modulate the sensitivity of cells to radiation therapy and to modulate cell proliferation and apoptosis.

BACKGROUND OF THE INVENTION

Human immunodeficiency virus type 1 (HIV-1) is a lentivirus that encodes the canonical retroviral Gag, Pol, and Env proteins, as well as six regulatory or auxiliary proteins including Tat, Rev, Vpu, Vif, Nef, and Vpr. Although not essential for viral replication in tissue culture, the latter four proteins are highly conserved and likely exert important but less well understood functions in vivo that contribute to viral pathogenesis. Vpr, a ~14-kDa, 96-amino acid protein is conserved among the primate lentiviruses HIV-1, HIV-2, and the simian immunodeficiency virus (SIV), supporting the notion that it serves an important function in the viral life cycle in vivo.

Human immunodeficiency virus (HIV) Vpr contributes to nuclear import of the viral preintegration complex and induces G2 cell-cycle arrest in infected proliferating T lymphocytes. Vpr is highly cytotoxic in pro- and eukaryotic cells and forms homo- and heterologous protein complexes, characteristics that limit the production of recombinant Vpr. Although partial sequences of Vpr have been synthesized for biological (25, 26) and structural studies (32, 33, 34), chemical synthesis of full-length soluble forms of Vpr has proven difficult. Others (27) have reported that Vpr is difficult to synthesize due to its tendency for incomplete coupling, matrix interaction and peptide aggregation. For example, a Vpr peptide derived from the HIV-1$_{BRU}$ sequence has been synthesized, but irreversible aggregation precluded purification of the product (38, 39, 40). The biological activity of such forms of Vpr could not be analyzed in solution. There remains a need for a protocol for high-yield production of synthetic Vpr (sVpr), in which the resultant protein remains both soluble and stable in aqueous solution.

In addition, there remains a need for vehicles capable of delivering molecules into cells. Given that Vpr contains at least two nuclear localization signals (3, 4, 5, 6, 7) and is capable of delivering molecules to the cell nucleus, a vehicle having the nuclear delivery capability of Vpr and also capable of efficiently entering the plasma membrane, preferably without requiring denaturation, is desirable.

SUMMARY OF THE INVENTION

The invention meets the above needs and others by providing a composition comprising a Vpr polypeptide conjugated to a therapeutic molecule. In preferred embodiments, the Vpr comprises synthetic Vpr. The synthetic Vpr is preferably stable in aqueous solution, such as the synthetic Vpr produced by the method described herein. The therapeutic molecule can comprise any molecule capable of being conjugated to a Vpr polypeptide, including a second polypeptide, a polynucleotide, and/or a toxin. The toxin can be selected or modified so as to be toxic only to a target cell population. In one embodiment, the toxin or other molecule is modified by conjugation to a regulatory molecule, wherein contact with a target cell affects the regulatory molecule in such a manner as to result in activation of the toxin. For example, the regulatory molecule may be recognized by a protease expressed in the target cell population. Upon contact with a target cell, the protease cleaves the Vpr-toxin conjugate, resulting in activation of the toxin.

The invention additionally provides a method for delivering a molecule into a cell. The method comprises contacting the cell with a conjugate comprising a Vpr polypeptide conjugated to the molecule. The invention further provides a method for modulating the expression of a transgene in a cell. The method comprises contacting the cell with a Vpr polypeptide conjugated to a regulatory molecule. The Vpr-:regulatory molecule conjugate, upon contact with the cell, enters the cell and the regulatory molecule modulates the expression of the transgene. In addition, the invention provides a method for killing a target cell population in a subject. The method comprises administering to the subject a Vpr polypeptide:toxin conjugate to the subject. In one embodiment, the toxin is an anti-proliferative agent and the target cell population is cancer cells. The target cell population may be a type of cell that is more susceptible than non-target cells to transduction by Vpr, or it may be a type of cell that is more susceptible than non-target cells to the toxin. In some embodiments, the toxin is further conjugated to a regulatory molecule. Upon contact with a target cell, the regulatory molecule is affected in such a manner as to result in activation of the toxin. In some embodiments, the target cell has been modified to contain a transgene or transgene product whose expression is regulated by the regulatory molecule. In this manner, the invention provides a method for modulating the expression of a transgene in the context of a gene therapy method that results in the killing of cells targeted by a gene therapy protocol.

The invention further provides compositions comprising Vpr, preferably sVpr. Such compositions include pharmaceutical and vaccine compositions, and can be used in a variety of methods. In one embodiment, the invention provides a method for increasing an immune response to an antigen in a subject exposed to the antigen comprising administering Vpr to the subject. The Vpr can be a Vpr polypeptide, and can be administered alone, together with the antigen, or as a Vpr:antigen conjugate. In another embodiment, the invention provides a method for increasing an immune response to HIV in a subject comprising administering a Vpr polypeptide to the subject.

In yet another embodiment, the invention provides a method for increasing the sensitivity of cells to radiation therapy. The invention additionally provides a method for inhibiting cell proliferation. The methods comprise contacting the cells with Vpr. Vpr acts synergistically with radiation to cause G2 arrest in cells, thereby providing a radiosensitizer for use in radiation treatment, such as for treatment of malignancies and other disorders associated with dysregulated cell growth. Vpr can also act alone to inhibit cell proliferation, thereby providing a treatment for hyperproliferative cell disorders, such as malignancies, psoriasis and other disorders associated with dysregulated cell growth. In addition, Vpr can induce apoptosis, and thus can be used in a method of killing cells.

BRIEF DESCRIPTION OF THE FIGURES

FIGS. 1A–G. Synthesis, purification, and MS analysis of sVpr and the C-terminal fragment $Vpr^{47-96}$. (1A) Primary sequence of sVpr derived from the isolate HIV-$1_{NL4-3}$ is shown (SEQ ID NO: 1) below the model of secondary structures identified in Vpr fragments (32, 35). Positively or negatively charged residues at the termini and helical structures, and a leucine-rich (LR) zipper-like motif that is presumably involved in the oligomerization of Vpr are indicated. Chromatograms of crude (1B) or purified (1C) sVpr obtained by reverse-phase acetonitrile gradient HPLC are shown, with UV detection at 214 nm. Positive-ion ESI mass spectra of purified sVpr: experimental mass spectrum showing the distribution of multiply charged ions (1D). Deconvoluted mass spectrum showing the intense envelope of the molecular ion at 11377.9 Da (1E). Experimental ESI mass spectra (1F) and chromatogram (1G) of purified $Vpr^{47-96}$.

FIGS. 6A–B. 2D $^1$H TOCSY spectrum of sVpr. NH region of the 2D TOCSY spectrum of sVpr in 50% TFE (6A) and in water alone (6B) displayed to show the sharp signals. Signal assignments are those described in the text.

FIGS. 7A–D. Cellular uptake and intracellular localization of sVpr-488. Fluorescently labeled peptide sVpr-488 at a concentration of 0.1 $\mu$g/ml was added to human macrophages (7A and 7B) or HeLa cells (7C and 7D). After 48 hours, cells were fixed and examined by phase-contrast (7A) and epifluorescence (7B) microscopy or by scanning confocal microscopy using phase contrast (7C, top) or epifluorescence (7C, bottom, and 7D).

FIGS. 10A–E. Cell transduction and nuclear import of sVpr. (10A–B) Macrophages visualized using standard microscopy. (10C–E) HeLa cells visualized using confocal imaging.

FIGS. 12A–F. sVpr transduces from the extracellular compartment into cells. Graphs plot counts for cells exposed to mock (A), Cy3 alone (B), $p6^{gag}$-Cy3 (25 $\mu$g/ml) (C), sVpr-Cy3 (2 $\mu$g/ml) (D), sVpr-Cy3 (5 $\mu$g/ml) (E), and sVpr-Cy3 (10 $\mu$g/ml) (F).

FIGS. 13A–B. sVpr induces G2 cell cycle arrest. Cells transduced with sVpr-Cy3 (B) show a greater proportion of cells in G2/M compared to Cy3 negative cells (A).

FIGS. 15A–E. sVpr tranduces Jurkat T cells and induces a dose-dependent G2 cell cycle arrest. sVpr subpopulations are identified based on FL1-H: Alexa-488 (15A). sVpr dose-dependent G2 arrest is shown by comparison of number of cells in G1/G0 versus G2/M as indicated by propidium iodide for non-transduced (15B), transduced subpopulation A (15C), transduced subpopulation B (15D), and transduced subpopulation C (15E).

FIG. 21. The carboxy terminal import signal (SEQ ID NO: 2) of Vpr contains a bipartite, arginine-rich motif, as shown in this schematic.

DETAILED DESCRIPTION OF THE INVENTION

Figure 2A:
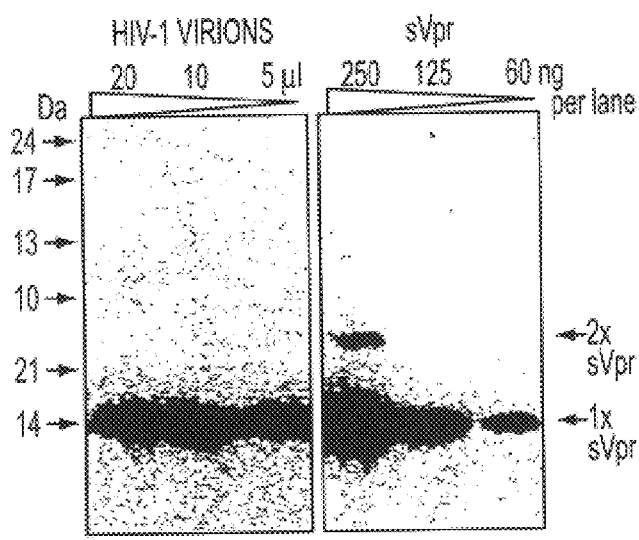
FIGS. 2A–C. Characterization of sVpt by SDS-PAGE, Western blot, and immunoprecipitation. (2A) A serial dilution of 250 to 60 ng of sVpr, or 20 to 5 $\mu$l of lysates of HIV-1 virions per lane were separated by SDS-PAGE on 16% gels, transferred to PVDF membrane, and stained with R-96 antibodies. Antibody binding was visualized by ECL reaction. Positions of molecular weight standard marker proteins are indicated to the left, positions of monomers and dimers of sVpr are indicated to the right. (2B) Silver-stained 18% SDS-PAGE after separation of 250 and 100 ng of sVpr in the presence or absence of 250 mM DTT. (2C) sVpr (0.1 to 10 ng) was mixed with human serum and immunoprecipitated with R-96 antibodies. Immunoprecipitates were separated by SDS-PAGE on 14% gels, electrotransfered, and analyzed by Western blot with R-96 antibodies and $^{125}$I-protein G for detection. On the right panel, sVpr (0.01–10 ng per lane) was directly separated in the gel before Western blot analysis. Autoradiograms of a 2-day-exposure are shown in both panels.

The present invention is based on the discovery that synthetic Vpr (sVpr) enters cells when added to the culture media, and that this cell entry occurs in a receptor-independent manner. sVpr enters cells efficiently, in nanomolar quantities, and without requiring denaturation. Because Vpr is immunogenic and also because it transduces cells, Vpr can be used as a vaccine (e.g., as an HIV vaccine) and/or as a vaccine adjuvant. For such uses, Vpr can be administered alone or conjugated to a second molecule, such as a protein, DNA or RNA. The invention further relates to the discovery that Vpr inhibits cell proliferation, induces apoptosis, and also acts synergistically with radiation to cause G2 arrest of cells, thereby providing a method for inhibiting cell proliferation, for inducing apoptosis or cell killing, and for enhancing sensitivity to radiation therapy.

Definitions

All scientific and technical terms used in this application have meanings commonly used in the art unless otherwise specified. As used in this application, the following words or phrases have the meanings specified.

As used herein, "Vpr polypeptide" means a protein or polypeptide having the cell transducing activity of Vpr. Vpr polypeptides and functional fragments thereof are identified in WO99/09412 and in German patent applications 199 08 752.0 and 199 08 766.0, filed on Feb. 19, 1999 and Feb. 17, 2000, respectively, as well as the corresponding PCT international patent application filed on Feb. 17, 2000.

As used herein, "subject" or "host" refers to the recipient of the therapy to be practiced according to the invention. The subject can be any vertebrate, but will preferably be a mammal. If a mammal, the subject will preferably be a human, but may also be a domestic livestock, laboratory subject or pet animal. For example, subjects can be bovine, ovine, porcine, equine, canine or feline.

As used herein, "native", in the context of nucleotide or amino acid sequence, refers to wild type or unaltered sequence.

As used herein, "analogous codon" means a codon that encodes the same amino acid, but may comprise a different triplet of bases.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parentetal administration are phosphate buffered saline or normal (0.9%) saline.

Compositions comprising such carriers are formulated by well known conventional methods (see, for example, Remington's Pharmaceutical Sciences, Chapter 43, 14th Ed., Mack Publishing Co., Easton Pa. 18042, USA).

As used herein, "a" or "an" means one or mote, unless clearly indicated otherwise.

Structure and Preparation of sVpr

The Vpr polypeptide for use in the invention is preferably synthetic Vpr (sVpr), and most preferably has the features of sVpr prepared in accordance with the methods disclosed in the Examples portion of the specification. Other methods of sVpr preparation may be used, but care should be taken to avoid protein aggregation. Preferably, the sVpr is soluble and stable in aqueous solution. Unlike other transducing proteins, sVpr does not require urea denaturation. Moreover, the transducing activity of sVpr is not enhanced by urea denaturation. Also unlike other transducing proteins, Vpr does not contain an arginine-rich transducing domain that functions in the absence of other portions of the protein. Thus, Vpr or sVpr in its native state is preferred. Those skilled in the art appreciate, however, that minor modifications, including substitutions and deletions, can be made to the Vpr without interfering with the biological activity of Vpr.

Administration and Dosage

In a preferred embodiment of the method, the Vpr or Vpr conjugate is administered via a systemic, enteral or topical route. Examples of systemic routes include, but are not limited to, intradermal, intramuscular, subcutaneous and intravenous administration. Examples of topical routes include, but are not limited to, intranasal, intravaginal, intrarectal, intratracheal, transdermal and ophthalmic administration. Examples of enteral routes include, but are not limited to, oral and gastric administration.

The Vpr or Vpr conjugate can be administered as a composition for treatment. Because treatment includes prophylaxis and therapy, the compositions of the invention include both pharmaceutical and vaccine compositions. Prophylaxis or therapy can be accomplished by a single direct administration at a single time point or multiple time points. Administration can also be delivered to a single or to multiple sites.

The subject can be any vertebrate, but will preferably be a mammal. Mammals include human, bovine, equine, canine, feline, porcine, and ovine animals. If a mammal, the subject will preferably be a human, but may also be a domestic livestock, laboratory subject or pet animal.

The dose of Vpr or Vpr conjugate to be administered to a subject, in the context of the present invention, should be sufficient to effect a beneficial therapeutic response in the subject over time, or to alleviate symptoms. Thus, the conjugate or composition is administered to a patient in an amount sufficient to alleviate, reduce, cure or at least partially arrest symptoms and/or complications from the disease. An amount adequate to accomplish this is defined as a "therapeutically effective dose."

Although the dosage used will vary depending on the clinical goals to be achieved, a suitable dosage range can be derived by reference to other references relating to Vpr and similar molecules, such as WO99/09412 and U.S. Pat. No. 5,804,604. The invention provides compositions, both prophylactic and therapeutic, that optionally include a pharmaceutically acceptable carrier. The conjugates of the invention can be prepared in a variety of formulations, including conventional pharmaceutically acceptable carriers, and, for example, microbeads, microspheres, capsules designed for oral delivery, etc. The conjugate can optionally be administered in conjunction with a drug useful in the treatment of the subject's condition. Such additional agents can be administered separately or included in the conjugate composition.

In view of the teaching provided by this disclosure, those of ordinary skill in the clinical arts will be familiar with, or can readily ascertain, suitable parameters for administration of compositions according to the invention, including combination of conjugate administration with conventional treatments.

Methods

The invention provides a method for delivering a molecule into a cell. The method comprises contacting the cell with a conjugate comprising a Vpr polypeptide conjugated to the molecule. Because sVpr rapidly and strongly transduces freshly isolated primary human cells at nanomolar concentrations, the methods of the invention provide an attractive and effective means for delivery of a molecule into a cell.

The invention further provides a method for modulating the expression of a transgene in a cell. The method comprises contacting the cell with a Vpr polypeptide conjugated to a regulatory molecule. The Vpr:regulatory molecule conjugate, upon contact with the cell, enters the cell and the regulatory molecule modulates the expression of the transgene.

In addition, the invention provides a method for killing a target cell population in a subject. The method comprises administering to the subject a Vpr polypeptide:toxin conjugate to the subject. In one embodiment, the toxin is an anti-proliferative agent and the target cell population is cancer cells. The target cell population may be a type of cell that is more susceptible than non-target cells to transduction by Vpr, or it may be a type of cell that is more susceptible than non-target cells to the toxin. In some embodiments, the toxin is further conjugated to a regulatory molecule. Upon contact with a target cell, the regulatory molecule is affected in such a manner as to result in activation of the toxin. In some embodiments, the target cell has been modified to contain a transgene or transgene product whose expression is regulated by the regulatory molecule. In this manner, the invention provides a method for modulating the expression of a transgene in the context of a gene therapy method that results in the killing of cells targeted by a gene therapy protocol. In an alternative embodiment, the method of killing a target cell population comprises administration of a Vpr polypeptide, without necessarily conjugating the Vpr polypeptide to a toxin or other molecule. Because sVpr can induce apoptosis, those cells which are more susceptible than non-target cells to transduction by Vpr are selectively killed.

In one embodiment, the invention provides a method for increasing an immune response to an antigen in a subject exposed to the antigen comprising administering Vpr to the subject. The Vpr can be a Vpr polypeptide, and can be administered alone, together with the antigen, or as a Vpr:antigen conjugate. In another embodiment, the invention provides a method for increasing an immune response to HIV in a subject comprising administering a Vpr polypeptide to the subject. As discussed in the examples below, CD4+, CD8+ and CD3− lymphocytes as well as CD14+ monocytes are equivalently transduced by sVpr. Thus, the delivery of Vpr and/or a Vpr:antigen conjugate to these cells can be particularly useful in the induction or enhancement of an immune response to HIV or other antigen.

In yet another embodiment, the invention provides a method for increasing the sensitivity of cells to radiation therapy. The invention additionally provides a method for inhibiting cell proliferation. The methods comprise contacting the cells with Vpr. Vpr acts synergistically with radiation to cause G2 arrest in cells, thereby providing a radiosensitizer for use in radiation treatment, such as for treatment of malignancies and other disorders associated with dysregulated cell growth. Vpr can also act alone to inhibit cell proliferation, thereby providing a treatment for hyperproliferative cell disorders, such as malignancies, psoriasis and other disorders associated with dysregulated cell growth. In addition, Vpr can induce apoptosis, and thus can be used in a method of killing cells.

EXAMPLES

The following examples are presented to illustrate the present invention and to assist one of ordinary skill in making and using the same. The examples are not intended in any way to otherwise limit the scope of the invention.

Example 1

Production and Biological Activity of sVpr

This example describes a protocol for high-yield production of synthetic Vpr (sVpr), and demonstrates that the resultant protein remains both soluble and stable in aqueous solution even at the relatively high protein concentrations required for structural studies. Circular dichroism demonstrates that sVpr is unstructured at neutral pH. In contrast, under acidic conditions (pH <5.0) or after the addition of trifluorethanol (TFE), sVpr adopts α-helical structures. Dynamic light scattering reveals that sVpr forms dimers in aqueous TFE, and high-order aggregates in pure water. Analysis of a C-terminal fragment, $Vpr^{47-96}$, indicates that this subdomain participates in α-helix formation and self-association. $^1H$ NMR signals allows the assignment of N- and C-terminal residues, however, the central section of the molecule is obscured by self-association. These findings suggest that the in vivo folding of sVpr may require structure stabilizing interacting factors such as previously described interacting cellular and viral proteins or nucleic acids. Surprisingly, in biological studies it was found that sVpr is effectively taken up from the extracellular medium by cells and also effectively imported into the nucleus of these transduced cells. Extracellular addition of sVpr also induces G2 cell cycle arrest in HeLa cells. Together, these findings raise the possibility that circulating forms of Vpr observed in HIV-infected patients may exert biological effects on a broad range of host target cells.

Vpr has important biological properties that may facilitate viral replication, including the presence of at least two nuclear localization signals (3, 4, 5, 6, 7). Unlike most animal retroviruses, the primate lentiviruses are able to replicate efficiently in non-dividing cells. Although not essential for viral replication in T cells, Vpr significantly augments viral replication in terminally differentiated monocytes/macrophages in vitro, a function that probably relates to its karyophilic properties (3). Vpr is thought to participate in the import of the viral preintegration complex (PIC), facilitating its passage across the nuclear pore. This import may similarly involve the function of other karyophilic vital proteins including the $p17^{gag}$ Matrix and Integrase proteins (reviewed in 8, 9).

Vpr also induces G2 cell-cycle arrest in infected proliferating human T cells (reviewed in 8, 10, 11). Such G2 arrest may serve to induce an intracellular milieu that is more favorable for LTR directed transcription (12). In fact, sufficient quantities of Vpr are present within the viral particle to induce G2 arrest prior to the de novo synthesis of proviral derived proteins (13, 14). Other biological activities ascribed to Vpr include ion-channel formation (15), transcriptional activation of various heterologous promoters (16, 17, 18, 19), co-activation of the glucocorticoid receptor (20), regulation of cell differentiation (10) and induction of apoptosis (21, 22). The importance of these latter functions for maintenance of the HIV replicative life cycle and the induction of disease in the infected host remains uncertain.

The participation of Vpr in HIV-1 replication in macrophages suggests that selective interruption of Vpr function with small molecule inhibitors might yield a new class of antiviral agents. However, the design of effective Vpr antagonists requires more detailed knowledge of its molecular structure, function, and mode of action. The availability of essentially unlimited quantities of pure and biologically active Vpr could certainly accelerate progress in understanding its biological functions and propel the development of effective antagonists. Recombinant Vpr has been produced in insect cells infected with recombinant baculovirus. At concentrations as low as 100 pg/ml, the extracellular addition of recombinant Vpr activates HIV-1 replication in both leukemic cell lines and primary peripheral blood mononuclear cells (PBMC) (23, 24). Vpr has also been expressed as a glutathione Stransferase fusion protein in *Escherichia coli* (15). However, after cleavage from the fusion protein or when isolated at high concentrations, these Vpr preparations often undergo spontaneous aggregation. In addition, production of Vpr by recombinant genetics is limited by cytotoxic effects of the protein in both pro- and eukaryotic cells (25, 26).

This example describes the production of synthetic Vpr (sVpr), its purification to homogeneity, and the characterization of this synthetic protein by N-terminal sequencing, mass spectrometry (MS), and gel electrophoresis. In addition, the behavior of sVpr in aqueous solution under various conditions as analyzed by dynamic light scattering (DLS), circular dichroism (CD), and $^1$H nuclear magnetic resonance (NMR) spectroscopy is presented. Finally, the example demonstrates that sVpr is effectively taken up from the extracellular medium, is imported into the nucleus of such transduced cells, and produces G2 cell cycle arrest.

Materials and Methods

Peptide Synthesis and Purification

Synthesis was performed on a Perkin-Elmer MilliGen 9050 automated peptide synthesizer at a 0.09 mM scale on a TentaGel R PHB Ser(tBu) Fmoc resin (capacity 0.19 mmol $g^{-1}$) using the Fmoc/tBu strategy. The following side-chain protecting groups were used: 2,2,4,6,7-pentamethyldihydrobenzofurane-5-sulfonyl (Arg), t-butoxycarbonyl (Trp, Lys), t-butyl ether (Thr, Ser, Tyr), t-butyl ester (Asp, Glu) and trityl (Asn, Cys, Gln and His). Couplings were performed with N-[1H-benzotriazol(1-yl) (dimethylamino)methylene]-N-methylnethanaminium hexafluorophosphate-N-oxide (HBTU), except that 1-(1pyrrolidinyl-1-H-1,2,3-triazolo-[4,5-b-]-pyridin-1-ylmethylene)-pyrrolidinium hexafluorophosphate-N-oxide (HAPyU) was used for the last 30 amino acids. Coupling was performed with 1 mmol Fmoc amino acids using HBTU in N-methylpyrrolidone as coupling agent with a cycle time of 45 min for single coupling and 75 min for double coupling applied for the last 56 amino acids. In order to increase the efficiency of the final part of the synthesis HAPyU (48) was used instead of HBTU as coupling reagent. In order to avoid aspartimide formation deprotection of the N-terminal Fmoc group was performed with pipetidine/DMF/formic acid during the entire course of the synthesis. Deprotection of the Fmoc group was performed during the complete synthesis with 20% piperidine in DMF, containing 0.1 M HCOOH to avoid aspartimide side reactions. The crude protein was purified by reverse phase HPLC on a VYDAC C18 column (40×300 mm, 1520μ, 300 Å) with a linear gradient of 100% A to 100% B in 53 min. (A, 1000 ml of water, 2 ml of TFA; B, 500 ml of acetonitrile, 100 ml water, 1 ml of TFA) at a flow rate of 100 ml min$^{-1}$ with spectrophotometric monitoring at λ=220 nm. The fractions were analyzed by HPLC (Shimadzu L10) on a VYDACC 18 column (4.6×250, 5μ, 300 Å) with a linear gradient of 10 to 100% B over 45 min. The peptide $Vpr^{47-96}$ was synthesized under the same condition, the synthesis of peptide $Vpu^{32-81}$ has been described (37).

Fluorescent Labeling of sVpr sVpr was labeled with Alexa 488 labeling kit (A-10235, Molecular Probes). The manufacturer's procedure was modified as follows: 2 mg of sVpr was dissolved in 1 ml of dimethyl formamide (DMF), 1 vial of dye from the kit was added, and the pH was adjusted to 8.5–9.0 with di-isopropyl ethylamine. After a 2-hr incubation at room temperature, the reaction was diluted with water, and the pH was adjusted to 2.0. Labeled sVpr was purified on the resin supplied with the kit. For flow cytometry, sVpr was labeled with the fluorescent dye bis-1,1'-(4-sulfobutyl)indodicarbocyanine-5-carboxylic acid (sodium salt) that was coupled in the last step of the peptide synthesis onto the N-terminal $NH_2$ of sVpr by incubating the resin with the peptide in DMF with HBTU and di-isopropyl ethylamine overnight. After completion, the resin was washed with DMF and methylene chloride, dried, and treated with 90% trifluoracetic acid (TFA) and 5% triisopropylsilane in water. TFA was then removed under vacuum, and sVpr was precipitated with diethyl ether purified by a standard HPLC procedure. This procedure selectively labels the N-terminal residue, leaving other side chains of the peptide functional, and allows a relatively easy purification of the peptide while still attached to the resin. Similar to Cy3, this novel fluorescent dye absorbs at 550 nm and emits at 585 nm. Its detailed synthesis will be described elsewhere.

Peptide Sequencing and Mass Spectrometry

For sVpr, 30 sequencing steps were completed on an Applied Biosystems 473A pulsed-liquid-phase sequencer according to a standard protocol. Positive-ion ESI mass spectra were recorded on a triple quad Finnigan TSQ 700 mass spectrometer equipped with an electrospray source. Protein samples were dissolved in 70% aqueous methanol and infused at a flow rate of 1 µL min$^{-1}$ into the electrospray chamber with an ES needle voltage of 5.5 kV. The experimental spectrum showing multiply charged molecular ions with 8 to 13 positive charges was deconvoluted with standard software. MALDI/TOF mass spectra were recorded on a Bruker reflex MALDI/TOF mass spectrometer using an $N_2$ laser (337 nm).

Circular Dicbroism (CD) Spectroscopy

CD spectra were recorded at room temperature in 0.5 mm cuvettes on a Jasco J-600 CD spectropolarimeter in a range 180 to 260 nm, and the resulting curves were smoothed with a high-frequency filter. Secondary structure content was quantified with the program VARSELEC.

$^1$H NMR Spectroscopy

Samples of the protein were dissolved in distilled water containing 10% $D_2O$ or containing 50% aqueous TFE-D2 by volume to give a final volume of 0.6 ml. Spectra were recorded at 300° K on a Bruker AVANCE DMX 600 NMR spectrometer. The $^1$H spectra were referenced to sodium 4,4-dimethyl-4-silapentane-1-sulphonate or internally to the residual methylene signal of TFE at 3.95 ppm. 2D phase-sensitive spectra of $^1$H COSY (correlation spectroscopy), TOCSY (total correlation spectroscopy) with mixing times 110 ms, and NOESY (nuclear Overhauser and exchange spectroscopy) with mixing times 250 ms, were recorded without spinning and processed with standard Bruker software.

Light-scattering Measurements

DLS was performed on a DynaPro-801 Molecular Sizing Instrument. Protein solutions (250 µl) prepared either in water or in 50% aqueous TFE at a concentration of ~3 mg ml$^{-1}$ (sVpr) or 4 mg ml$^{-1}$ (Vpr$^{47-96}$) were injected through a 0.1-µm Whatman membrane filter. Samples were illuminated by a semiconductor laser (780 nm, 25 mW) generated by a miniature solid-state $Ga_{1-y}Al_yAs$-diode. The photons scattered at a 90° angle by the particles in the sample were collected by an avalanche photodiode, and the time-dependent fluctuation in intensity of the scattered light was analyzed. The translational diffusion coefficient DT was calculated with the manufacturer's software (Dynamics, version 2.1). DT was then used to calculate the degree of sample polydispersity and the hydrodynamic radius of gyration RH of the particles using the Stokes-Einstein equation: $(R_H=(k_bT)*(6\pi\eta D_T)^{-1}$ where $k_b$=Boltzman's constant, T=absolute temperature in Kelvin, and η=solvent viscosity). $M_r$ was calculated on a standard curve ($M_r$ vs. $R_H$) supplied by the manufacturer. Ten continuous measurements were made for each sample.

Antibodies, SDS-PAGE, Western Blot, and Immunoprecipitation

A rabbit polyclonal antiserum, R-96, was generated by immunization with sVpr. Immunoprecipitation of sVpr was carried out in Triton wash buffer (50 mM Tris/HCl, pH 7.4, 60 mM NaCl, 0.5% Triton X100), precleared with non-immune human and rabbit sera, followed by incubation with R-96 antibodies pre-loaded onto GammaBind-Plus-Sepharose beads. The immunoprecipitates were washed twice with Triton wash buffer, once with SDSDOC buffer (50 mM Tris/HCl, pH 7.4, 300 mM NaCl, 0.1% SDS, 0.1% deoxycholate), boiled for 10 min at 95° C. in sample buffer (2% SDS, 1% mercaptoethanol, 1% glycerol, 65 mM Tris/HCl, pH 6.8), and subjected to electrophoresis on 16% PROSIEVE SDS-PAGE gels. Virus stocks were generated in HeLa cells transfected with pNL4-3 (49) and subsequently used to infect MT 4 cells. Virions were pelleted from cell culture supernatant (30,000× g, 1.5 hrs, 4° C.) and purified on a sucrose cushion. For immunoblotting, samples were transferred to Immobilon polyvenylidene difluoride (PVDF) membranes (Immobilon). Membranes were incubated with R-96 and binding of the antibodies was identified with $^{125}$I-labeled protein G.

Cellular Uptake of sVpr sVpr and Vpu$^{32-81}$ were iodinated with the chloramine-T method. Briefly, ~20 µg of peptides were reacted with 5.5×10$^7$ Bq (1.5 mCi) Na$^{125}$I. Free iodine was removed by gel filtration through a Dowex ion-exchange column saturated with bovine serum albumin (BSA). For studies on cellular uptake, rat yolk choriocarcinoma L2-RYC cells were grown in Dulbecco's modified Eagle's medium (DMEM) with 10% (v/v) fetal bovine serum (FBS) to 75% confluence on 24-well plates. Cells were washed once with phosphate-buffered saline (PBS) and incubated in serum-free DMEM supplemented with 0.1% BSA and $^{125}$I-labeled sVpr or, as a negative control, $^{125}$I-labeled Vpu$^{32-81}$. Radioactive peptides were added to the medium at a specific activity of 18 kBq ml$^{-1}$. In parallel, cells were also treated with a 100-fold excess of unlabeled sVpr or Vpu$^{32-81}$. Cells were incubated for specified times at 37° C., and the distribution of intra- and extracellular radioactivity was determined as described (50). Briefly, medium was removed, and the cell layer was washed with PBS and lysed with 1% Triton X-100 in PBS. Radioactivity was determined in triplicate in the medium and cell layer. To correct for nonspecific binding of peptides to the cell surface, the cell layer radioactivity determined at time point 0 min (time when radiolabeled peptides were added to the medium for less than 30 sec) was subtracted as background from the radioactivity detected in the cell layer.

For cellular localization studies, either a suspension of HeLa cells (2×10$^6$ ml$^{-1}$) or a confluent monolayer of human macrophages cultivated in chamber slides was incubated with fluorescent sVpr-488. After 48 hours, the cells were washed with PBS, fixed with 1% paraformaldehyde for 10 min, and mounted. The specimens were examined by epifluorescence or scanning confocal microscopy (model MRC-600; Bio-Rad Labs). Macrophages were isolated from random HIV-1-seronegative healthy blood donors. First, PBMC were isolated using Ficoll-Paque (Amersham) and grown in slide chambers, containing DMEM, 100% FCS, and 10% human serum AB (Gemini Bio-Products). After 1 week, cells were washed, and the adherent monolayer of monocyte-derived macrophages was used for import studies with sVpr. The number of cells transduced by sVpr-Cy3 was estimated by flow cytometry.

Cell Cycle Analysis

HeLa cells were incubated with sVpr-Cy3 for 48 hrs, trypsinized, and fixed for 30 min in 2% formaldehyde followed by incubation with 1 mg ml$^{-1}$ RNaseA and 10 µg ml$^{-1}$ propidium iodide in PBS for 30 min. Cellular DNA content in the fixed cells was then assessed with a FACScan flow cytometer and analyzed with the ModFit LT program (Beckton Dickinson).

Results

Synthesis and Purification of sVpr

Solid-phase peptide synthesis (SPPS) of full-length Vpr was performed with a sequence derived from the isolate HIV-1$_{NLA-3}$ (FIG. 1A). HPLC profiles of the crude and purified protein products are shown in FIGS. 1B and 1C, respectively. In contrast to a recently described SPPS procedure for the synthesis of a Vpr protein derived from a different HIV-1 isolate (27), the procedure was optimized as described herein with respect to the use of coupling agents, protection groups, cleavage reagents, and duration of coupling reactions. The present protocol gave reproducibly high yields (usually 15%) of purified sVpr without encountering any of the previously reported (27) synthesis problems such as incomplete coupling and deprotection, inter- and intrachain reaction with the resin matrix, hydrogen bond mediated peptide aggregation, or side chain reactions. Various fragments of sVpr were also synthesized using the same SPPS protocol. The HPLC purification of the peptide $Vpr^{47-96}$, comprising the C-terminal domain of sVpr from positions Tyr-47 to Ser-96 is demonstrated in FIG. 1G.

Analysis of sVpr by Protein Sequencing, MS, and Western Blotting

The identity of purified sVpr was confirmed by sequencing of the N-terminal 30 amino acids. Positive-ion electrospray ionization (ESI) MS was used for molecular weight determination. The experimental data showed a well-defined multiply-charged spectrum (FIG. 1D) that was deconvoluted to give an intense envelope for the molecular ion cluster at a molecular weight of 11377.9 Da (FIG. 1E), corresponding exactly with the molecular weight of 11377.9 Da calculated for sVpr. In addition, the correct molecular weight of sVpr was also established by matrix-assisted laser desorption/ionization time-of-flight (MALDI/TOF) MS which showed an intense molecular ion cluster at 11377.2 Da (not shown). In summary, the MS and sequence analyses indicated that sVpr was homogenous and showed no detectable evidence of by-products. Similar results were also obtained for the C-terminal fragment $Vp^{47-96}$. The peptide was purified to homogeneity (FIG. 1G) and the correct molecular weight of 5829.7 Da was established by ESI MS (FIG. 1F).

Figure 2B:
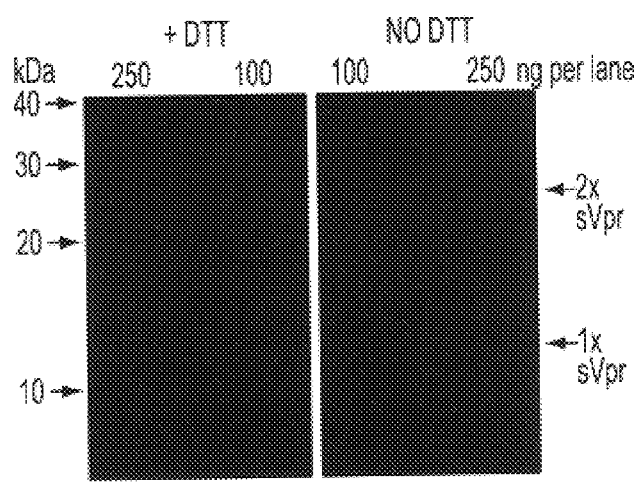
Figures 1, 9A:
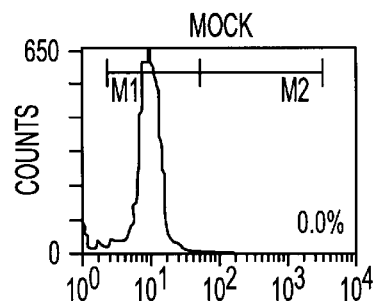
FIGS. 9A–B. sVpr transduction and induction of G2 cell-cycle arrest. (9A) HeLa cells were incubated in medium containing sVpr-Cy3 or similarly labeled $p6^{gag}$-Cy3 at the indicted concentrations, fixed and stained with propidium iodide, and analyzed by flow cytometry. There was a dose-dependent uptake of sVpr-Cy3 while no $p6^{gag}$-Cy3 was found staining the cells. (9B) Cell-cycle analysis of HeLa cells incubated with 2 $\mu$g/ml of sVpr-Cy3 shows significantly more Cy3-positive cells than Cy3-negative cells in the G2/M phase.
Figures 2, 9A:
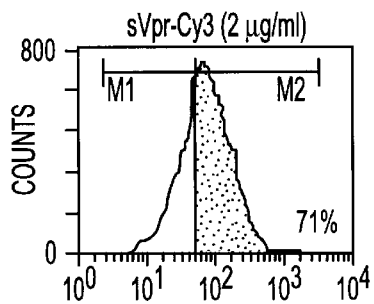

Molecular properties of sVpr were further characterized by SDS-PAGE (FIG. 2). Dilutions of sVpr were separated and detected by Western blotting using Vpr specific antibodies. For comparison with viral Vpr, lysates of purified HIV-1 particles were analyzed in parallel (FIG. 2A). In agreement with sequencing and MS data, sVpr migrated as a single band with an apparent molecular mass of ~14 kDa that was almost indistinguishable from the migration of viral Vpr. Peptide fragments that could result from proteolysis or incomplete synthesis were not detected by Western blot (FIG. 2A) or direct silver staining of sVpr in SDS-PAGE (FIG. 2B).

In addition to monomeric Vpr, a small percentage of sVpr was detected in an Mr range consistent with dimers and, trimers. Such candidate oligomers were only detected at concentrations of ≧250 μg sVpr per lane (FIG. 2A). The fact that sVpr forms multimers (as shown below by DLS) is consistent with the previous demonstration of Vpr oligomers by chemical cross linking (28). These multiple forms were not observed with preparations of viral Vpr (FIG. 2A). Two possibilities may explain these results. First, according to the detection of monomeric sVpr by Western blot, the highest amount of viral Vpr analyzed corresponded to ~125 ng of sVpr per lane; at this concentration multimers of sVpr were not detected. Second, physical interactions between the C-terminal $p6^{gag}$ domain of the Pr55 Gag polyprotein (29, 30) direct the incorporation of Vpr into budding virus particles (31). Hence, the presence of at least one of the known Vpr binding partners, $p6^{gag}$, in the virus preparation may prevent homo-oligomerization of vital Vpr that was otherwise evident for isolated sVpr.

Figure 2C:
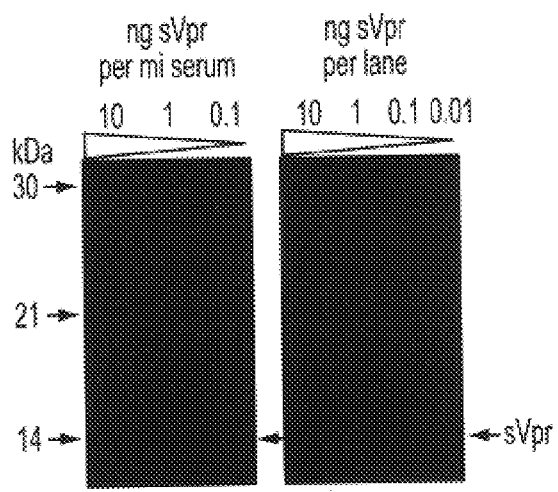

Vpr contains a single cystein at residue 76 that may potentially participate in intermolecular disulfide bond formation. Although disulfide-bridged dimers have not been reported for viral or recombinant Vpr, SDS-PAGE analysis of sVpr in the absence of reducing agents indicated that ~10% of the molecules exist as disulfide-linked dimers, the formation of these dimers was prevented by the addition of dithiothreitol (DTT) (FIG. 2B).

sVpr was also used as an immunogen in rabbits to generate polyclonal anti-Vpr antibodies. The titer of the anti-Vpr antibody, R-96, was significantly increased when standard coupling of sVpr to keyhole limpet hemocyanin was omitted. The resultant R96 antiserum reacts with Vpr proteins from several different HIV-1 isolates and binds to both virus-derived Vpr and svpr with comparable efficiency. Furthermore, using R96 for immunoprecipitation sVpr was detected at concentrations as low as 10 ng ml$^{-1}$ diluted in human serum (FIG. 2C). Together, this demonstrates the usefulness of R96 for detection of vital Vpr in serum samples of HIV-infected individuals (23).

DLS Analysis of Vpr

The SDS-PAGE results (FIGS. 2A,B) and the previously published cross-linking data (28) suggest that isolated Vpr tends to form oligomeric structures. To study the multimerization of sVpr in its dynamic state in solution, as opposed to the artificial fixation of particular folding states by chemical cross-linking, DLS was used to examine sVpr under various solution conditions. In pure water at a concentration of 3.8 mg ml$^{-1}$ without pH adjustment (pH 3.0), deconvolution of the primary DLS data indicate the existence of at least two main components with RH values of ca. 4.8 nm and 26.2 nm (with relative abundance of 14% and 86%) corresponding to complexes with molecular weights of 128 kDa and 8075 kDa, respectively. Thus, in aqueous solution, sVpr existed as high-order aggregates (>500-mers) with a lower percentage of smaller oligomers. Such high-order complexes of sVpr cannot be resolved by SDS-PAGE and may not be stabilized by cross-linking. Although the majority of sVpr exists in high $M_r$ aggregates, no precipitation of the peptide was observed, even at concentrations as high as 4 mg ml$^{-1}$.

Next tested was whether multimers of sVpr could be reduced by an organic solvent such as TFE, which favors intramolecular interactions and suppresses hydrophobic intermolecular interactions that were implied to drive Vpr clustering (32). DLS data acquired in 50% TFE showed that sVpr exists as a single species with a particle size that deviates less than 15% from the average $R_H$ of 2.3 nm. This value corresponds well to a molecular mass of 26 kDa and indicates that TFE induces the formation of stable sVpr dimers. Thus, the addition of TFE promotes a substantial loss of high-order aggregates and the formation of dimers. This could result from changes in secondary structure that reduce the tendency for aggregation or from suppression of hydrophobic interactions by TFE.

Recently, it was suggested that a leucine-rich (LR) domain located within the third, C-terminal α-helix of Vpr provides the molecular constraints for homo-oligomerization of Vpr (32). Therefore investigated was whether the C-terminal fragment, $Vpr^{47-96}$, also tends to self-associate. DLS analysis of $Vpr^{47-96}$ in pure water showed a single component (98.5% abundance) with an RH value of ~3 nm corresponding to a hexameric particle of ~43 kDa. Upon addition of 50% TFE, one major species (94.2% abundance) of monomer ($R_H$=1.25, 6.25 kDa) and small amounts of dimers and trimers were detected. These data indicate, that like full length sVpr the C-terminal fragment Vpr$^{47-96}$ exhibits an inherent tendency for oligomerization that depends on the hydrophobicity of the solvent.

Characterization of sVpr by CD Spectroscopy

Figure 3A:
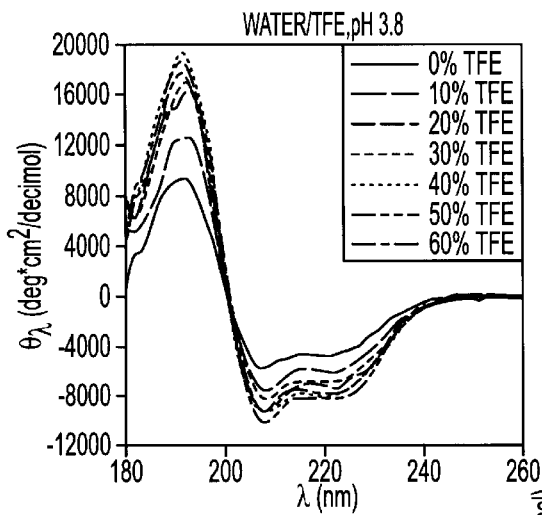
FIGS. 3A–D. Far-ultraviolet CD spectra of sVpr. Spectra were recorded in pure water at different TFE concentrations (3A) and at different pH values in $P_i$ buffer alone (3B) or with 20% (3C) or 50% TFE (3D).

To further analyze the effect of TFE on secondary structures in sVpr, the peptides were investigated by CD spectroscopy under various solution conditions. Initially, sVpr was analyzed in water alone, without buffer, at a pH of ~3.8. The corresponding CD curve demonstrated negative ellipticity at 208 and 222 nm, and a strong positive band at ~192 nm (FIG. 3A). These findings suggested the presence of significant content of α-helical structure, accounting for ~18% according to deconvolution of the CD spectrum. Addition of up to 20% TFE resulted in an initial stabilization of these helical structures (up to ~31% helical content) while further addition of TFE up to 60% induced smaller changes with the maximum helical content at approximately 50% TFE. In contrast to previous studies of Vpr protein fragments (32, 33, 34, 35), the findings described herein suggest that sVpr possesses structure even in pure water and that its helical structure is stabilized but not induced by TFE.

Figure 3B:
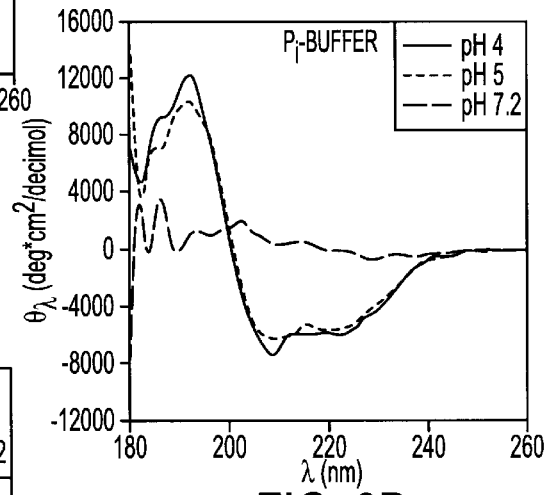

Compared to the calculated basic isoelectric point, it was surprising that solutions of sVpr adopt a helical configuration at acidic pH since this is inconsistent with the physiological pH present in the cytosol or nucleus of the cell where Vpr is predominantly expressed. Hence, sVpr was analyzed at a constant concentration in phosphate buffer ($P_i$) while varying the pH from 3.9 to 7.2 (FIG. 3B). Remarkably, while increasing pH up to 5.0 had almost no effect, at neutral pH 7.2 the protein adopted a completely random conformation. This transition occurred at a critical pH of approximately 5.0, some loss in the shape of CD curves started at pH 6.0 (data not shown) while deprivation of structure was complete at neutral pH. In agreement with the DLS measurements, no precipitation of sVpr was evident under any of the solution conditions investigated.

Figure 3C:
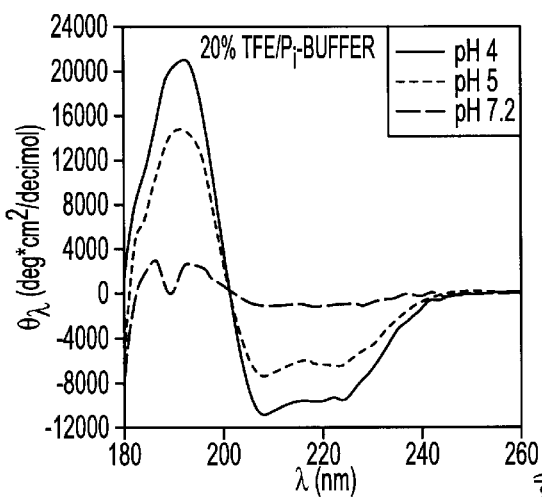
Figure 3D:
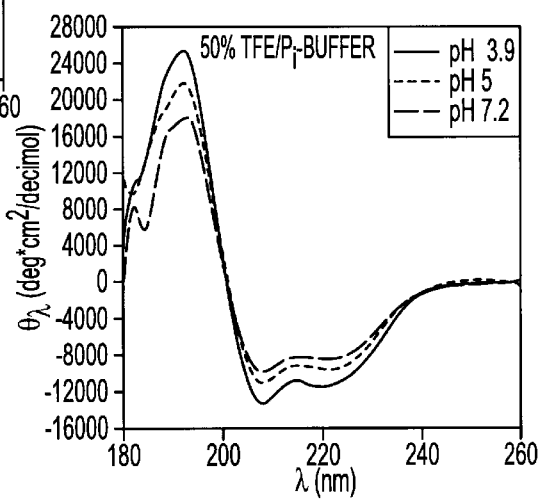

Subsequently tested was whether the destabilizing effect of neutral pH on sVpr structure could be reversed by addition of TFE, an agent that appears to have a subtle effect on the peptide structure at acidic pH. Addition of 20% TFE, which had near-maximal effect at pH 3.8 (FIG. 3A), did not stabilize svpr at neutral pH (FIG. 3C). However, TFE concentrations as high as 50% clearly provided an environment where the helical structure of sVpr was present (FIG. 3D), even at the critical neutral pH where sVpr exhibited no structure without TFE (FIG. 3B). In 50% TFE, the change from pH 4 to 7.2 had only a small effect upon the CD curves, implying that the secondary structure remained intact and was only slightly destabilized on transition to the higher pH (FIG. 3D).

Figure 4A:
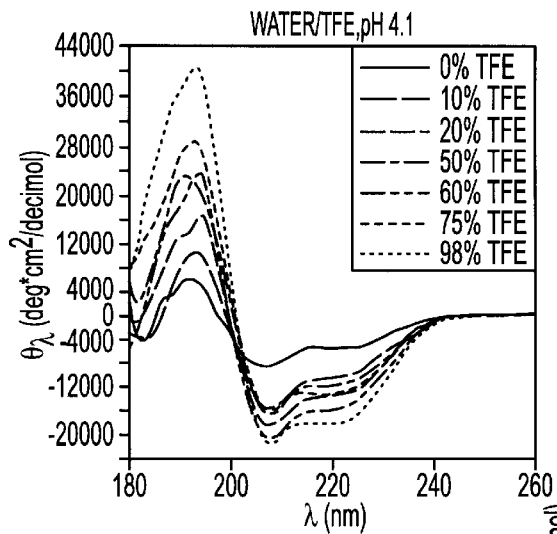
FIGS. 4A–D. Far-ultraviolet CD spectra of $Vpr^{47-96}$ recorded in pure water at different TFE concentrations (4A) and at different pH values in $P_i$ buffer alone (4B) or with 20% (4C) or 50% TFE (4D).
Figure 4B:
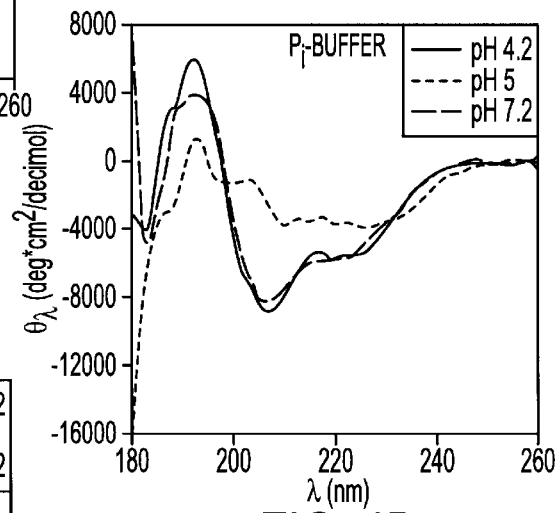
Figure 4C:
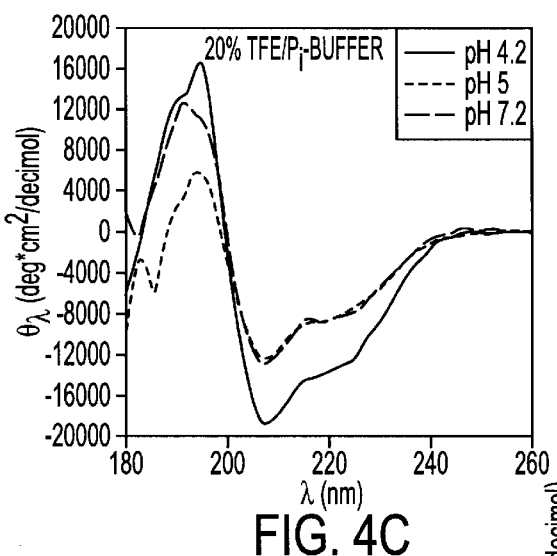
Figure 4D:
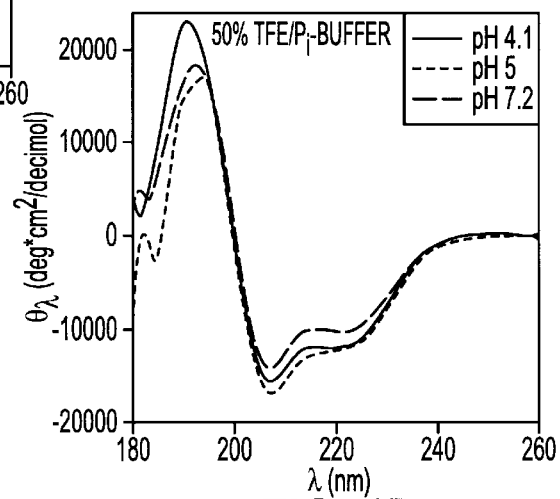
Figures 3, 9A:
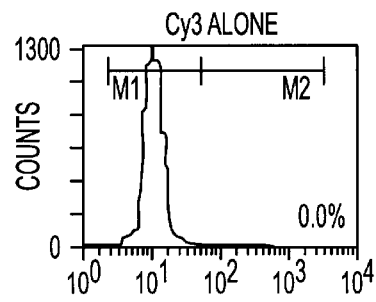
Figures 4, 9A:
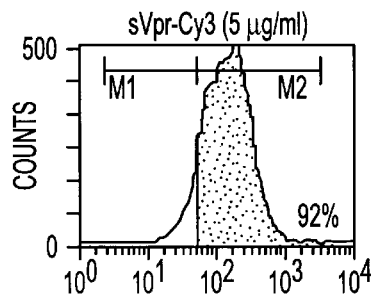

Recent structure studies on a 51-residue N-terminal fragment of Vpr revealed no consequences of pH variation on secondary structure (35). These findings implied that the structural motif contributing to the pH-dependent folding of sVpr (FIG. 3) may be located within the C-terminal domain of Vpr. To test this hypothesis, the fragment Vpr$^{47-96}$ (FIGS. 1F,G) was subjected to an identical CD analysis (FIG. 4). Like sVpr, Vpr$^{47-96}$ adopted an acidic pH of 4.1 in pure water and tended to have a helical conformation, although not as pronounced as sVpr (FIG. 4A). Addition of TFE increased the helical content, yet in contrast to sVpr, there was a linear response with TFE concentration that reached a maximum at 98% TFE. As with sVpr, a pH-dependent folding switch was observed for Vpr$^{47-96}$ at pH 5.0 (FIG. 4B). The effect of TFE was slightly different to the situation of sVpr as the unfolding of Vpr$^{47-96}$ could be reversed to some extent by the addition of 20% TFE (FIG. 4C). Again, in 50% TEE solution, the destabilizing effect of neutral pH was almost absent (FIG. 4D). Thus, the folding of the C-terminal fragment responded to changes in solvent conditions in a fashion similar to that of full-length sVpr.

In summary, solution conditions can profoundly affect the structure of full-length Vpr: The peptide is completely unstructured at neutral pH, while lowering the pH to a critical threshold of pH 5.0 or adding a membrane mimetic, such as TFE, stabilizes secondary structure that is mainly α-helical in character. This phenomenon can be attributed, at least partially, to structures located in the C-terminus, most likely in the LR-domain of Vpr.

$^1$H NMR Spectroscopic Characterization of sVpr

Figure 5A:
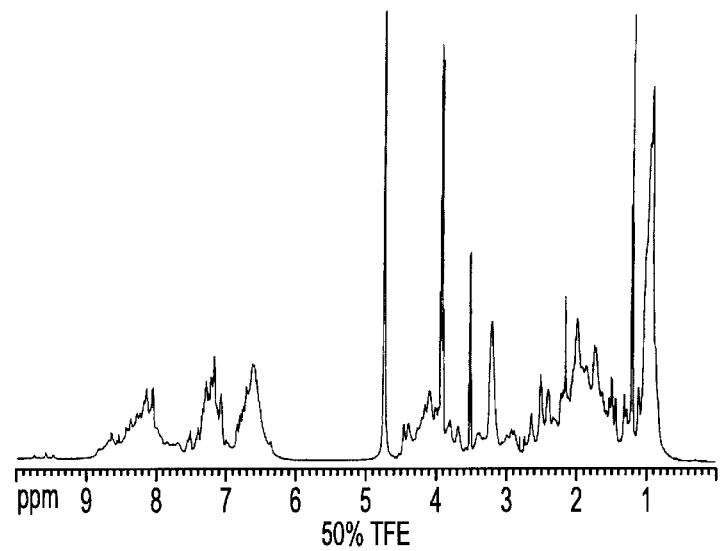
FIGS. 5A–C. 1D $^1$H NMR spectrum of sVpr. (5A) $^1$H NMR spectrum in 50% TFE. (5B) The low-field region of the same spectrum. (5C) The corresponding low-field region of the $^1$H NMR spectrum of sVpr in water alone.
Figure 5B:
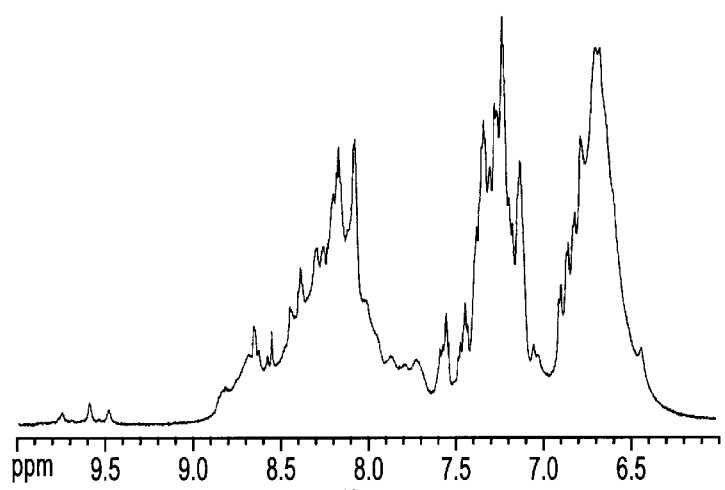
Figure 5C:
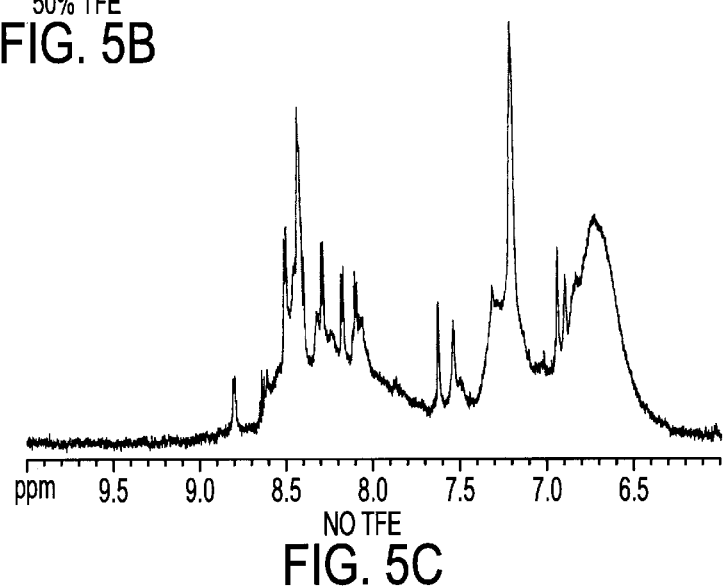
Figures 5, 9A:
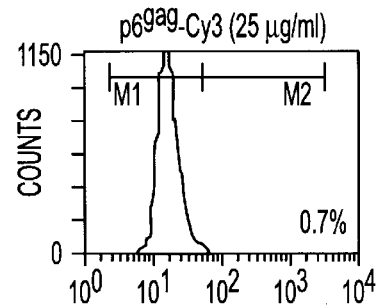

The structure of sVpr was further analyzed by $^1$H NMR spectroscopy under various solution conditions. 1D and 2D $^1$H NMR spectra were recorded in water alone without any salt or buffer at pH 3.1 and in TFE/H$_2$O (1:1). Stable solutions of sVpr devoid of any sign of protein precipitation were obtained at concentrations considerably higher than those employed in the CD measurements. The 1D spectra of sVpr (FIG. 5) showed relatively broad lines for both solutions, although the majority of those in water alone were the broadest. This is readily seen in the low-field region of the spectrum where line widths of 10–12 Hz were measured for the Trp-N$^1$H signals at 9.4–9.9 ppm in the 50% TFE solution (FIG. 5B), but these lines were not visible in the spectrum obtained in pure water (FIG. 5C).

SDS-PAGE analysis (FIG. 2B) indicated that a small fraction of sVpr forms disulfide-linked dimers. However, the addition of an equimolar amount of DTT gave no visible alteration in the NMR spectrum, suggesting that the majority of the molecules were not present as disulfide-linked dimers. However, it must be remembered that the NMR data were obtained using a protein solution at pH ~3, while the SDS-PAGE was performed at pH 6.8. Consequently the signal broadening (FIG. 5), indicative of protein—protein interaction, most likely arises from non-covalent associations for which a leucine-zipper motif in the C-terminus has been implicated (32).

Figures 6, 9A:
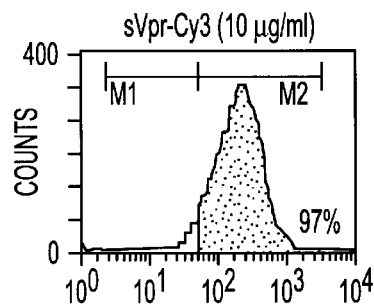

The 1D and 2D NMR spectra (FIGS. 5 and 6) show a further phenomenon: in both pure aqueous as well as 50% TFE solutions the protein has some regions that show particularly broad lines while at least several parts of the molecule appear to be relatively flexible resulting in sharper lines. Thus, inspection of 2D TOCSY spectra at different contour levels (FIG. 6) indicates that there are several residues with resolvable spin systems. NOESY spectra of sVpr in 50% TFE indicate that these signals belong to the first 7 N-terminal (Glu-2 to Gln-8) and 5 C-terminal (Gly-92 to Ser-96) residues of the protein (FIG. 6A). Similarly, in water alone and at a lower concentration of sVpr, the C-terminal residues Gly-82 to Thr-84 and Gly-92 to Arg-95 were unambiguously identified (FIG. 6B).

Extracellular sVpr Transduces Cells and Localizes to the Nucleus

Like the HIV-1 Tat protein, extracellular Vpr has been shown to posses biological activity. Recombinant Vpr or Vpr isolated from the serum of patients displaying high HIV-1 loads enhances viral replication in both infected cell lines and primary human PBMCs (23, 24). Further, recombinant Vpr added to cell culture medium appears to exert glucocorticoid like effects (22). However, it has not been formally determined whether virion-free Vpr actually enters cells or instead engages cell-surface receptors and initiates various signaling cascades. To address these questions and to test the biological activity of sVpr, cellular uptake and subcellular localization of sVpr were studied. The peptide was labeled with the fluorophor Alexa-488 (sVpr-488) to monitor its potential uptake and subcellular localization in both macrophages and HeLa cells. These studies revealed that sVpr-488 effectively entered cells following its addition in the extracellular medium (termed as protein transduction) and further accumulated in the nucleus of these transduced cells (FIG. 7). This intracellular staining pattern was not observed with a 10-fold higher concentration of a labeled control peptide (p6$^{gag}$-488) or the unconjugated fluorescent dye itself. Confocal microscopy revealed that in HeLa cells the transduced peptide sVpr-488 appears to be occasionally concentrated in cytosolic spots, while the majority of the peptide was clearly localized in the nucleus (FIGS. 7C,D). These data, together with the preliminary observation that sVpr activates HIV-1 replication and is specifically incorporated into budding HIV-1 virions, provide evidence that sVpr possesses biological activities similar to those of viral Vpr.

Receptor-independent Uptake of sVpr

Figure 8:
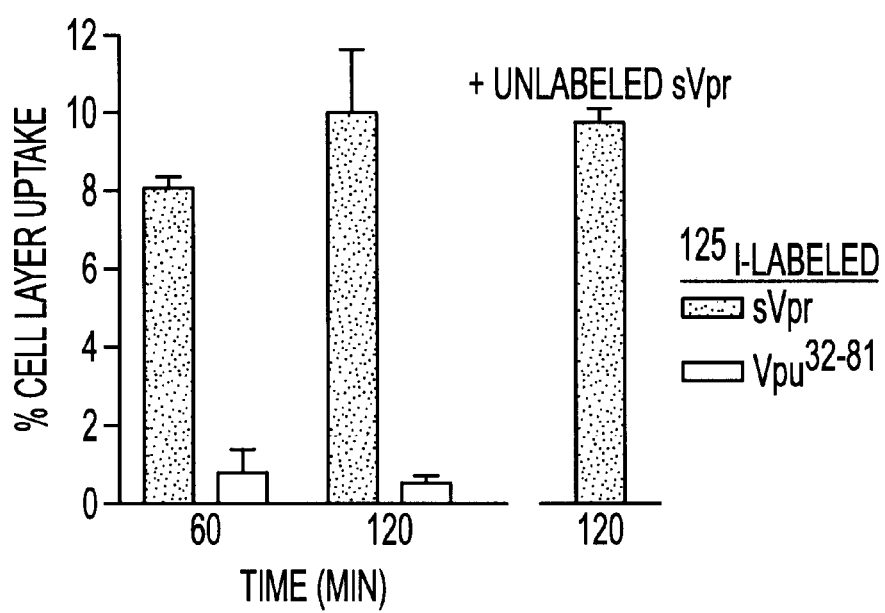
FIG. 8. Receptor-independent uptake of sVpr. L2 cells were incubated with $^{125}$I-labeled sVpr or $Vpu^{32-81}$ (control) for 60 or 120 min, and the distribution of radioactivity in the cell layer and the medium was determined in triplicate. In parallel, cells were incubated for 120 min with $^{125}$I-lableled sVpr and a 100-fold molar excess of unlabeled sVpr.

Next, the specificity of sVpr uptake was analyzed. Because Vpr is cationic, the possibility was considered that its uptake is mediated by megalin, a cell-surface receptor that is expressed in a variety of tissues and binds to positively charged molecules (36). In the carcinoma cell line L2-RYC, which expresses large amounts of megalin, significant and time-dependent uptake of sVpr was observed (FIG. 8). The level of intracellular sVpr reached a maximum of 8–10% within 2 hours followed by a constant plateau for up to 16 hours. This plateau may reflect a steady state between uptake and secretion of radioactivity. In contrast, a 50-amino acid control peptide, Vpu$^{32-81}$, synthesized under the same conditions as full length sVpr and containing similar secondary structural elements (37) was not effectively internalized (FIG. 8). Similar results were also obtained in HeLa cells.

Furthermore, the uptake of $^{125}$I-lableled sVpr was not inhibited by a 100-fold excess of unlabeled svpr (FIG. 8), suggesting that this process either does not involve a saturable receptor system or alternatively is mediated through a very high capacity receptor system.

sVpr is Transduced Efficiently and Induces G2 Cell-cycle Arrest

Figures 1, 2, 9B:
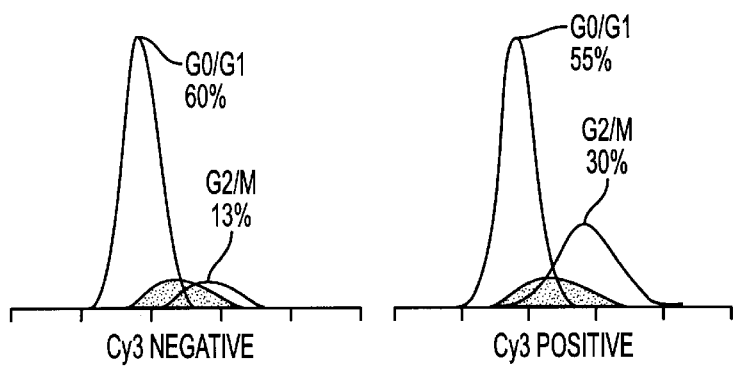

Transfection of various proliferating human cells with expression vectors encoding HIV-1 Vpr produces G2 cell-cycle in a majority of the transfected cells (10). Given the nucleophilic properties of sVpr, it was investigated whether cells transduced with extracellularly added sVpr undergo a similar cell-cycle arrest. HeLa cells were incubated with sVpr labeled with a Cy-3-like fluorophor that allows effective sorting of the transduced cells. When sVpr-Cy3 was added at concentrations of 2, 5, and 10 $\mu$g ml$^{-1}$, flow cytometric studies revealed dose-dependent uptake of sVpr-Cy3 from the medium (71%, 92%, and 97% of the cells, respectively) (FIG. 9A). When cells were incubated with sVpr-Cy3 at 2 $\mu$g ml$^{-1}$ and sorted based on fluorescence, 30% of the positive cells were arrested in the G2/M phase of the cell cycle. In contrast, only 13% of cells of the non-transduced cell population were present in G2/M (FIG. 9B). These data suggest that sVpr is biologically active and is able to induce G2 cell cycle arrest in susceptible cells.

Discussion

Synthesis of Full-length Vpr

Biological and structural studies of Vpr have been hampered by the limited availability of purified protein due to the inherent propensity of Vpr to participate in homo- and heteromolecular interactions leading to aggregation. Although partial sequences of Vpr have been synthesized for biological (25, 26) and structural studies (32, 33, 34), chemical synthesis of full-length soluble forms of Vpr has proven difficult. For example, a Vpr peptide derived from the HIV-1$_{BRU}$ sequence has been synthesized, but irreversible aggregation precluded purification of the product (38, 39, 40). The biological activity of such forms of Vpr could not be analyzed in solution. Far-Western blotting demonstrated the binding of SDS-denatured Vpr to the viral nucleocapsid p7$^{NC}$ (39), a finding not recapitulated with virus-derived Vpr (30). The optimized SPPS protocol described herein permits the synthesis of soluble Vpr in sufficient quantities to allow structural and biological analyses. This approach also circumvents the cytotoxic effects and attendant low yields obtained when Vpr is expressed in either prokaryotic or eukaryotic cells (21, 22, 25). While others (27) have claimed that Vpr is difficult to synthesize due to its tendency for incomplete coupling, matrix interaction and peptide aggregation, these difficulties were not encountered by this use of optimized Fmoc chemistry with no additional side chain protection.

Effect of Solution Conditions on Structure and Oligomerization of sVpr

Several attempts have been made to identify and characterize the structural and functional domains of Vpr. This protein appears to contain at least four discrete domains: a negatively charged N-terminus, a central domain comprised of three helices (N-terminal $\alpha$-1 and $\alpha$-2 and C-terminal $\alpha$-3), and a positively charged C-terminus (FIG. 1A). The best characterized region, $\alpha$-3 (residues 53–78), overlaps with a leucine-rich domain that contains a short leucine zipper-like motif involved in self-association (32, 41). The assignment of functional domains largely derives from mutational analyses and is complicated by variable results. Nuclear localization and cell cycle arrest have been assigned to different domains in Vpr although mutations throughout the length of Vpr can alter various properties of this protein (4, 25, 34, 41, 42). Structural analyses of Vpr fragments have relied on CD and NMR spectroscopy. In all cases, the membrane mimetic organic solvent TFE or micelle solutions were employed to obtain suitable solution conditions that afford structure-stabilizing effects. Full-length sVpr based on HIV-1$^{BRu}$ has been studied in 30% TFE, although structural details have not been reported (27).

The initial NMR experiments on sVpr in water alone and in 50% TFE identified line broadening for $^1$H signals from the central section of the molecule and 2D data allowed sequential assignments of only a limited number of C- or N-terminal residues. To gain further insights into the folding characteristics of sVpr, DLS and CD studies of sVpr were conducted in various solutions. In pure water and in the absence of other binding partners, sVpr formed large complexes that preserved a significant amount of $\alpha$-helical structure at low pH. Above pH 5.0, the structure became random. Remarkably, this pH-induced switch was minimized by the addition of TFE. Thus, TFE has three pronounced effects on sVpr: it prevents large complex formation, stabilizes secondary structure at low pH, and protects this secondary structure against disruption at physiologic pH. These characteristics are consistent with the tendency of Vpr to interact with other molecules, including cellular and viral proteins (reviewed in 8) or even HIV-1-derived DNA (32, 43). These interactions may, like TFE or pH, stabilize structure and folding of Vpr.

Cellular Uptake and Nuclear Translocation of sVpr

It was important to demonstrate that sVpr exhibited biological activities similar to that characteristic of virus-derived Vpr. Indeed, sVpr displayed nucleophilic properties similar to virus-derived Vpr or Vpr expressed in transfected cells. Furthermore, sVpr also induced G2 cell cycle arrest in human cells. Perhaps most surprisingly, sVpr mediated these effects even when added to the extracellular medium of cell cultures. Biological functions have been attributed to extracellular Vpr, but it was unknown whether Vpr actually can enter cells independent of the viral context. These findings are the first evidence that isolated molecules of Vpr alone can effectively transduce cells and exert a biological effect.

The HIV protein Tat has also been shown to contain an effective protein transduction domain (44, 45). Recent in vivo studies have demonstrated that Tat can promote cellular uptake of a variety of proteins fused to Tat in an array of different cells including the brain (46, 47). This finding suggests that Vpr and Tat share protein transduction properties. It is likely that the unusual dipole character of Vpr, in combination with the C-terminal basic residues, regulates binding of Vpr to charges on membrane phospholipids and that cell uptake may be mediated by amphipathic helices present in Vpr. The transduction domain of Tat has recently been localized to the sequence YGKKRRQRRR (SEQ ID NO: 4), which strongly resembles the motif RQRRAR (SEQ ID NO: 5) centered in the basic C-terminus of Vpr (44). Interestingly, this arginine-rich domain is sufficient for nuclear translocation of a heterologous cytoplasmic protein through a novel low energy, RanGTP-independent pathway of nuclear import (4). It has been proposed that there are at least two import signals contained within Vpr, one consisting of the leucine-rich helices and one present in the basic C-terminal region (4).

Transduction of cells by sVpr provides a novel mode of delivering proteins into the cytosol and the nucleus. This adds a new dimension to the possible role of cell transduction of designer proteins as therapeutic agents. Furthermore, this delivery system is quite efficient at nanomolar concentrations of sVpr and does not require a denaturation step, a procedure that sharply increases the efficiency of Tat mediated transduction (47). Of note, sVpr retains its karyophilic properties and is able to induce G2 cell cycle arrest in transduced cells. These findings add support to the notion that in vivo extracellular Vpr is biologically active and may even target host cells that can not be infected by HIV.

sVpr is highly immunogenic. sVpr was used to generate high-titer and broadly reactive polyclonal and monoclonal antibodies reacting with Vpr. Furthermore, sVpr activates HIV-1 replication in primary cells and is effectively incorporated into viral particles. This, together with the finding that sVpr is taken up from the extracellular medium, localizes to the nucleus, and induces G2 cell cycle arrest, generates confidence that the peptide prepared displays biological activity. The availability of significant amounts of biologically active sVpr should enable further studies aimed at clarifying the precise function of this viral protein, its mechanism of action, and its contributions to HIV pathogenesis.

Example 2

Further Elucidation of the Biological Activity of sVpr in HIV-1 Infected and Uninfected Cells Protein transduction is the ability to cross a biological membrane in a receptor-, energy-independent process. Helical wheel alignment of the C-terminal portion of Vpr revealed an arginine-rich face, similar to the transduction domains of other characterized transducing proteins. sVpr cellular uptake defined by trypsin insensitivity occurs effectively at 4° C., a property consistent with protein transduction previously described with the Drosophila antennapedia, HSV VP22, and HIV Tat proteins.

This example shows that sVpr is optimized for rapid protein transduction and is biologically active in HIV-1 infected and uninfected cells. Briefly, the results show that (1) separating the putative transducing domain from the remainder of the sVpr molecule does not result in a functional Vpr capable of transduction; (2) urea denaturation does not enhance the transduction properties of sVpr; (3) sVpr rapidly and strongly transduces freshly isolated primary human cells at nanomolar concentrations; (4) CD4+, CD8+ and CD3-lymphocytes and CD14+ monocytes are equivalently transduced by sVpr; and (5) sVpr induces apoptosis in cultured T cells.

Full length Vpr was chemically synthesized and fluorescently labeled, purified by reverse phase HPLC, and added to the extracellular media of various cell cultures. Flow cytometry and epifluorescence microscopy were employed to monitor cellular uptake of sVpr. The distribution of cells within different phases of the cell cycle was studied by To-Pro-3 dye staining of DNA followed by flow cytometric analysis. The results are summarized in FIGS. 10–29.

Figure 28:
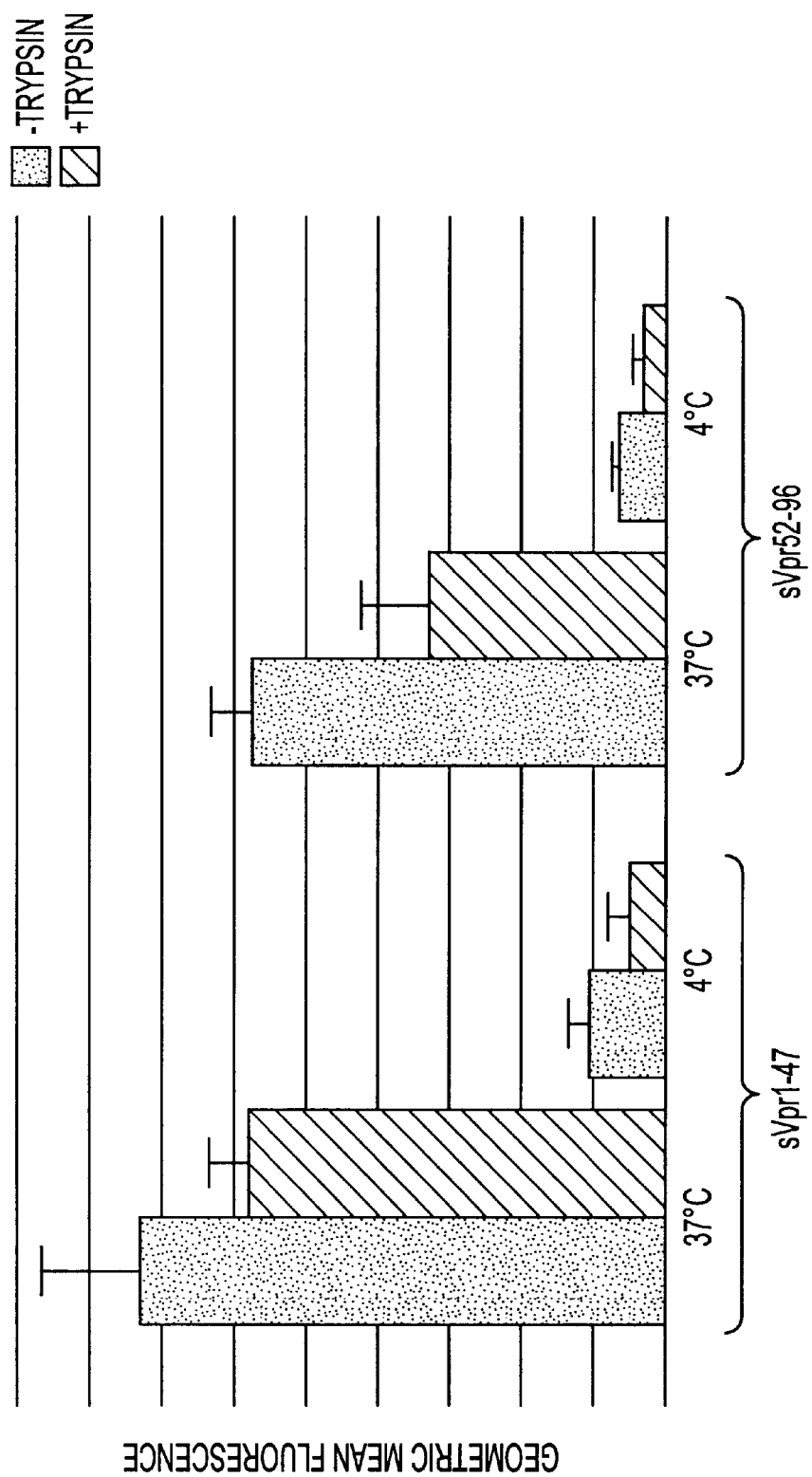
FIG. 28. Fragments of sVpr do not transduce. Geometric mean fluorescence is plotted for cells exposed to sVpr 1–47 or sVpr 52–96 at 37° C. or 4° C. in the presence or absence of trypsin.
Figure 29:
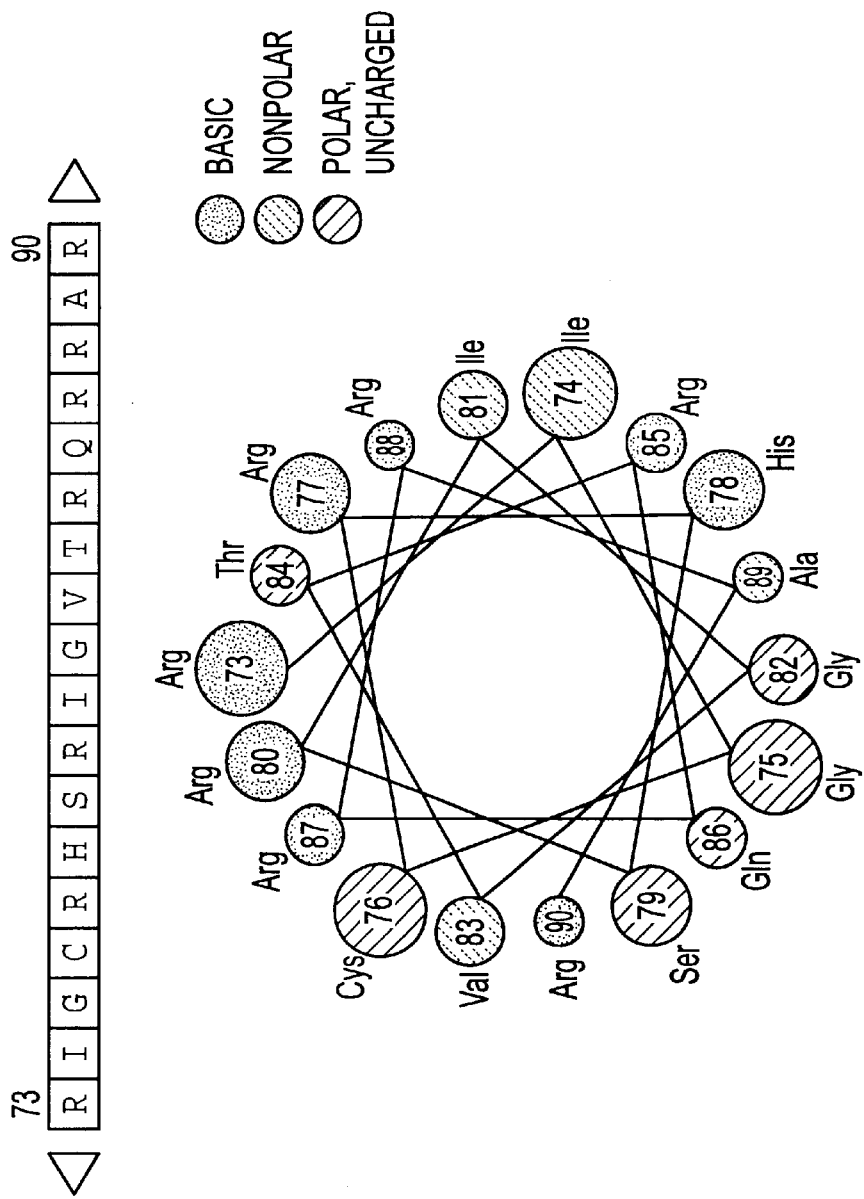
FIG. 29. Schematic demonstration that the arginine residues in the C-terminal domain of NL4-3 Vpr (SEQ ID NO: 3) align on a common face as predicted by an alpha helical wheel.

Surprisingly, studies mapping the transduction domain of svpr revealed that, in contrast to the previously identified transducing proteins, sVpr does not display an arginine rich transducing domain that functions in the absence of other portions of the protein. The ability of sVpr fragments, specifically residues 1–47 and 52–96 of sVpr, to transduce was studied and revealed that these fragments lack the transduction capability of full-length sVpr (FIG. 28). It appears that full-length sVpr, or at least more than only the putative transducing domain, is necessary for efficient protein transduction.

Figure 11:
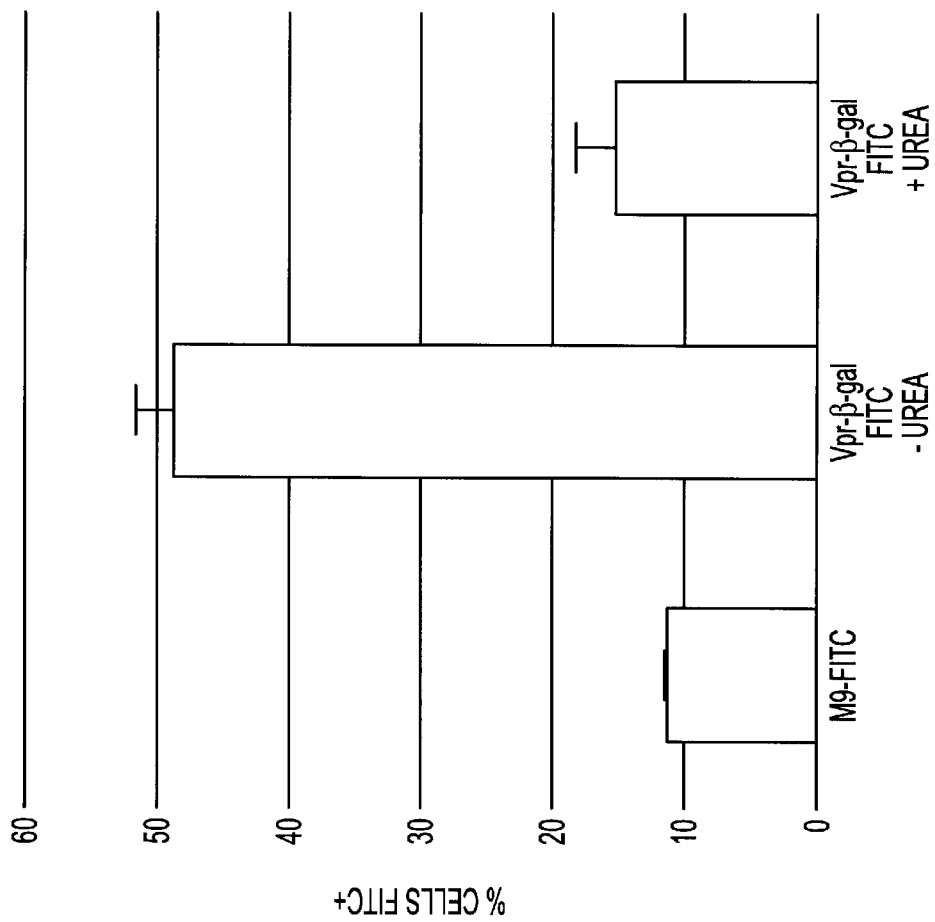
FIG. 11. Urea-denatured Vpr-β-galactosidase no longer transduces. Bar graph shows percent of cells FITC+ for M9-FITC controls and Vpr-β-gal FITC with and without urea treatment.
Figure 14A:
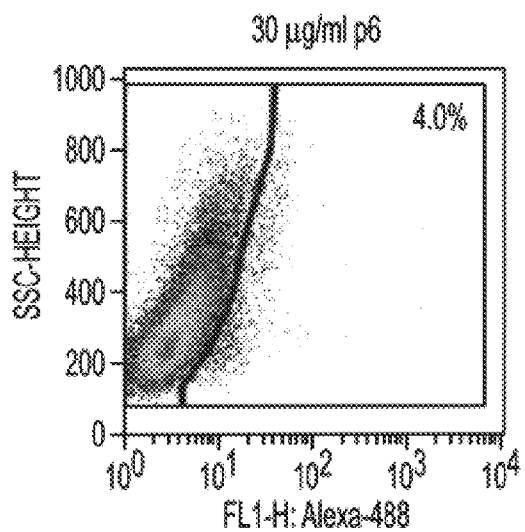
FIGS. 14A–D. sVpr tranduces Jurkat T cells in a dose-dependent fashion. SSC height is plotted as a function of FL1-H: Alexa-488 for 30 $\mu$g/ml $p^6$ (A), 7.5 $\mu$g/ml sVpr (B), 15 $\mu$g/ml sVpr (C), and 30 $\mu$g/ml sVpr (D).
Figure 14B:
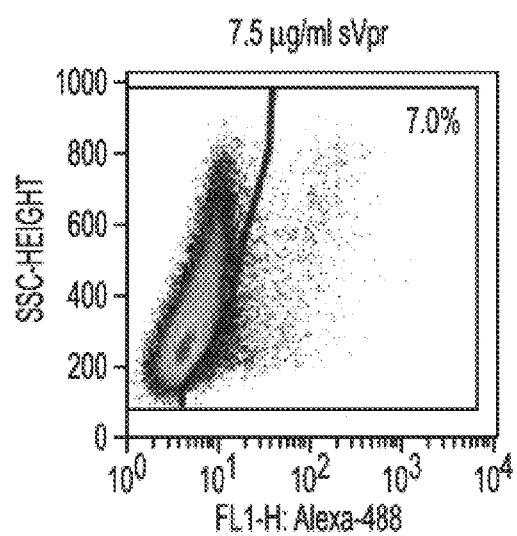
Figure 14C:
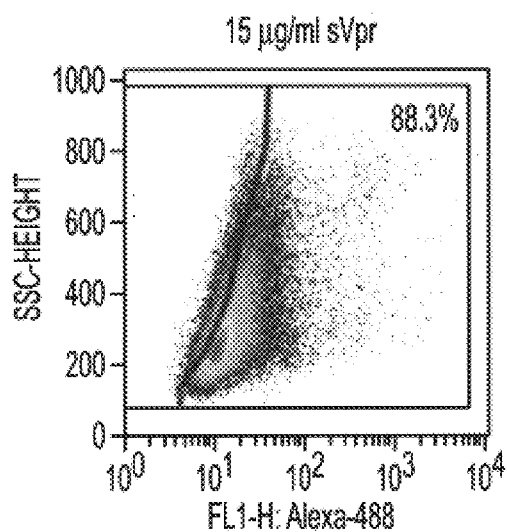
Figure 14D:
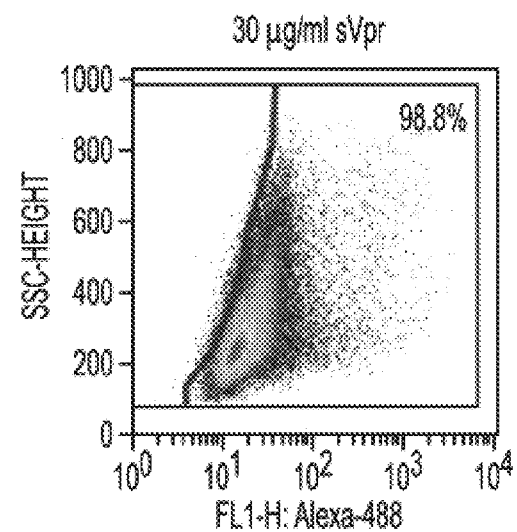
Figure 16A:
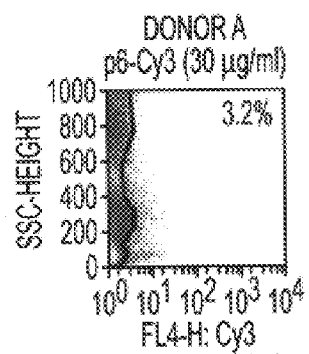
FIGS. 16A–H. sVpr tranduces peripheral blood mononuclear cells freshly isolated from healthy donors. Shown is SSC height as a function of FL4-H: Cy3 for PBMC isolated from donors A–D following exposure to p6-Cy3 at 30 $\mu$g/ml (16A–D) or sVpr-Cy3 at 30 $\mu$g/ml (16E–H).
Figure 16E:
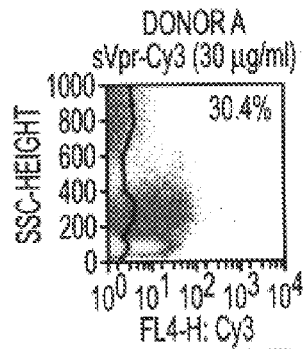
Figure 16B:
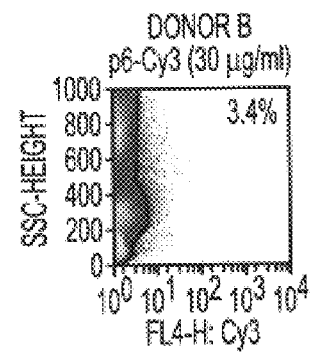
Figure 16F:
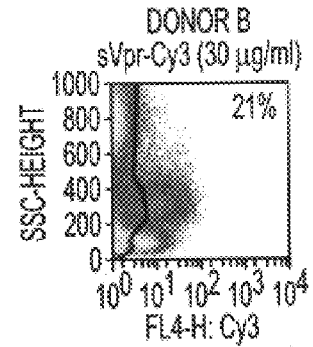
Figure 16C:
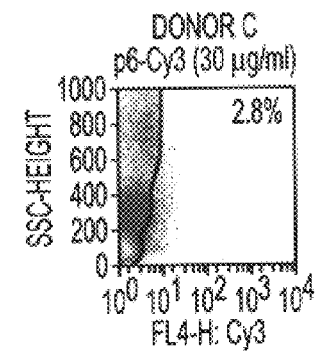
Figure 16G:
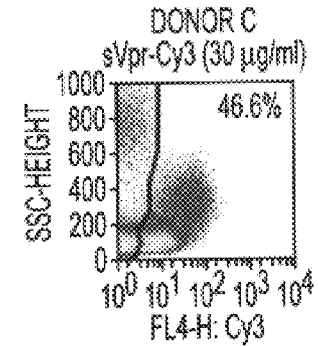
Figure 16D:
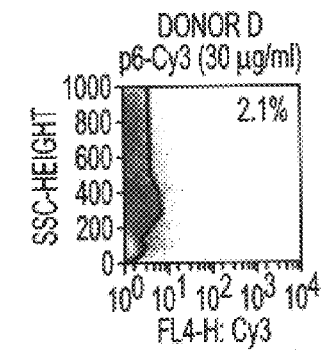
Figure 16H:
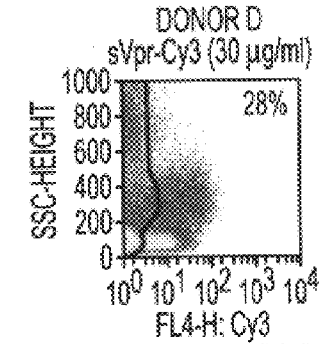
Figure 17:
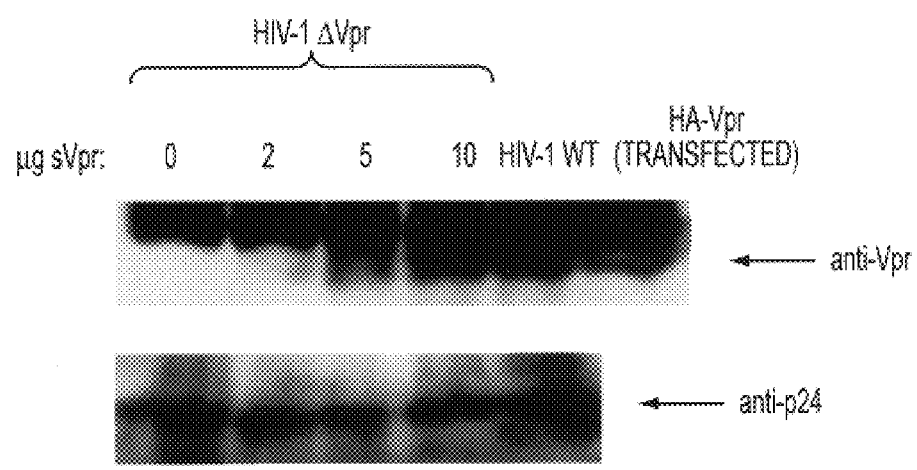
FIG. 17. sVpr is incorporated into newly produced HIV-1 virions. Shown is a western blot using anti-Vpr and anti-p24 antibodies, comparing HIV-1 vitions exposed to differing concentrations of sVpr.
Figure 18:
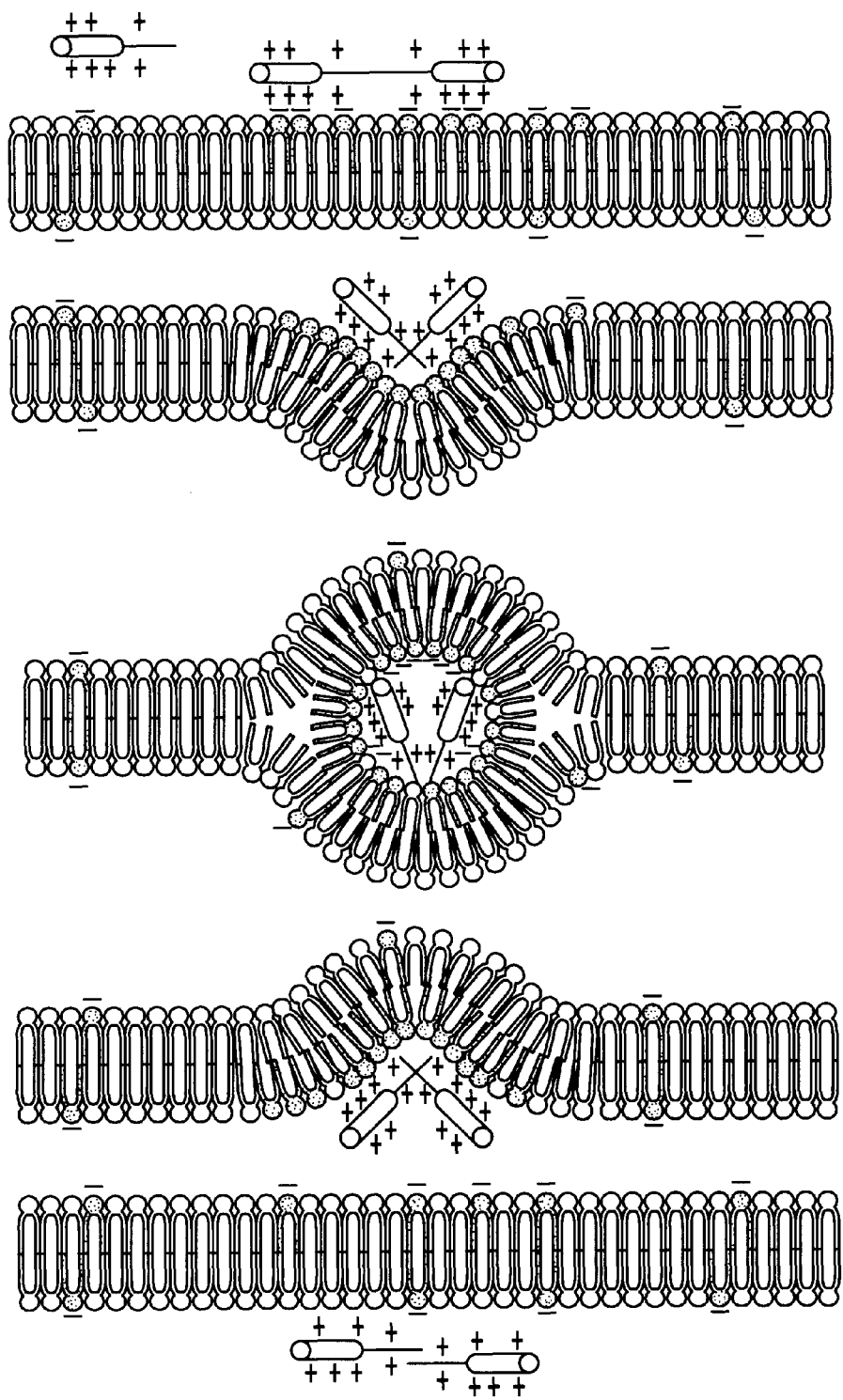
FIG. 18. Schematic diagram showing potential model for protein transduction based on charge characteristics; adapted from Derossi et al., JBC 1996; 271:18188.
Figure 19:
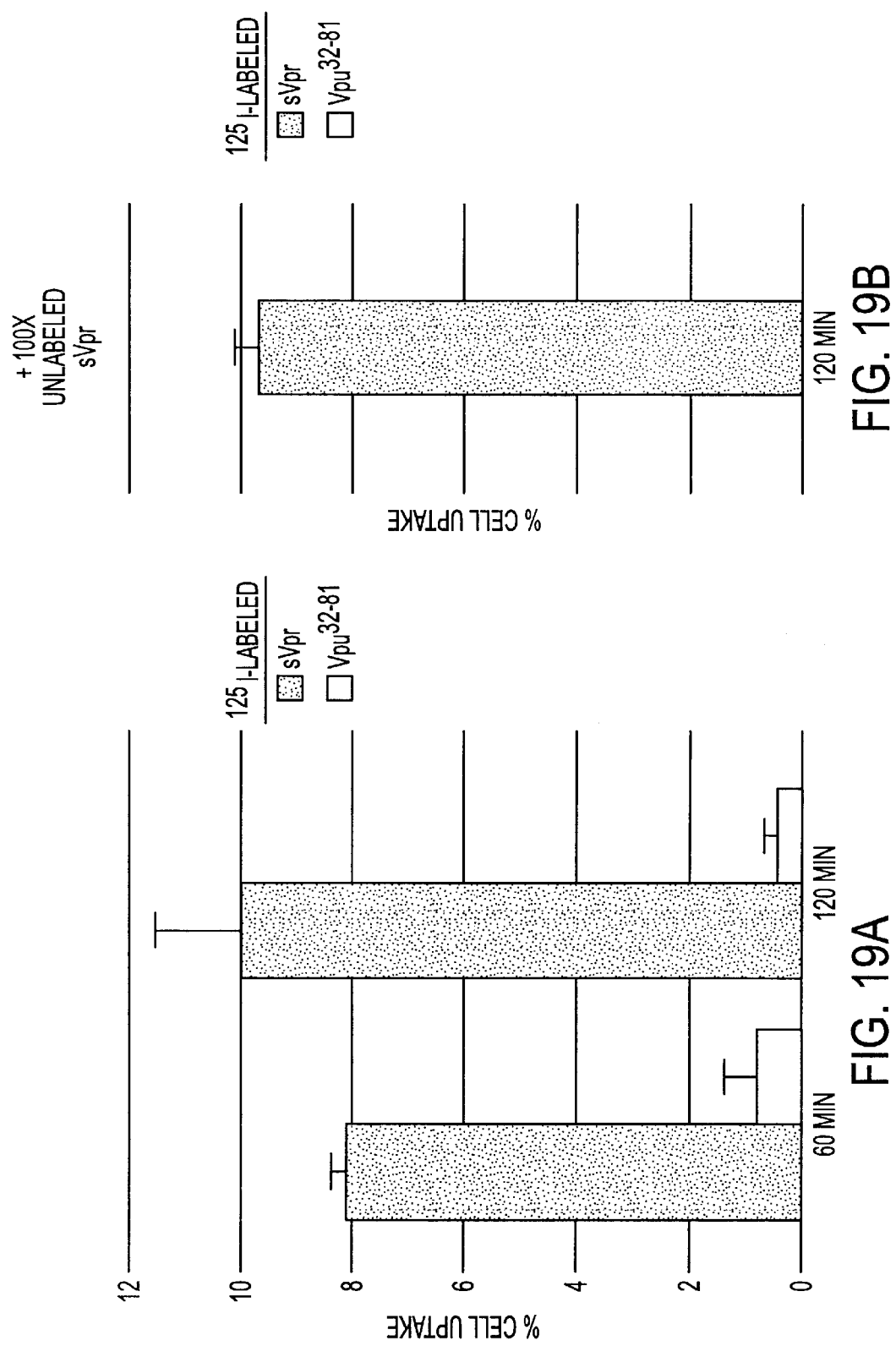
FIGS. 19A–B. sVpr cellular uptake is not inhibited in competition experiments. Percent cell uptake is plotted for 125I-labeled sVpr and Vpu$^{32-81}$ at 60 mm and 120 mm and compared to uptake with the addition of 100× unlabeled sVpr.
Figure 20:
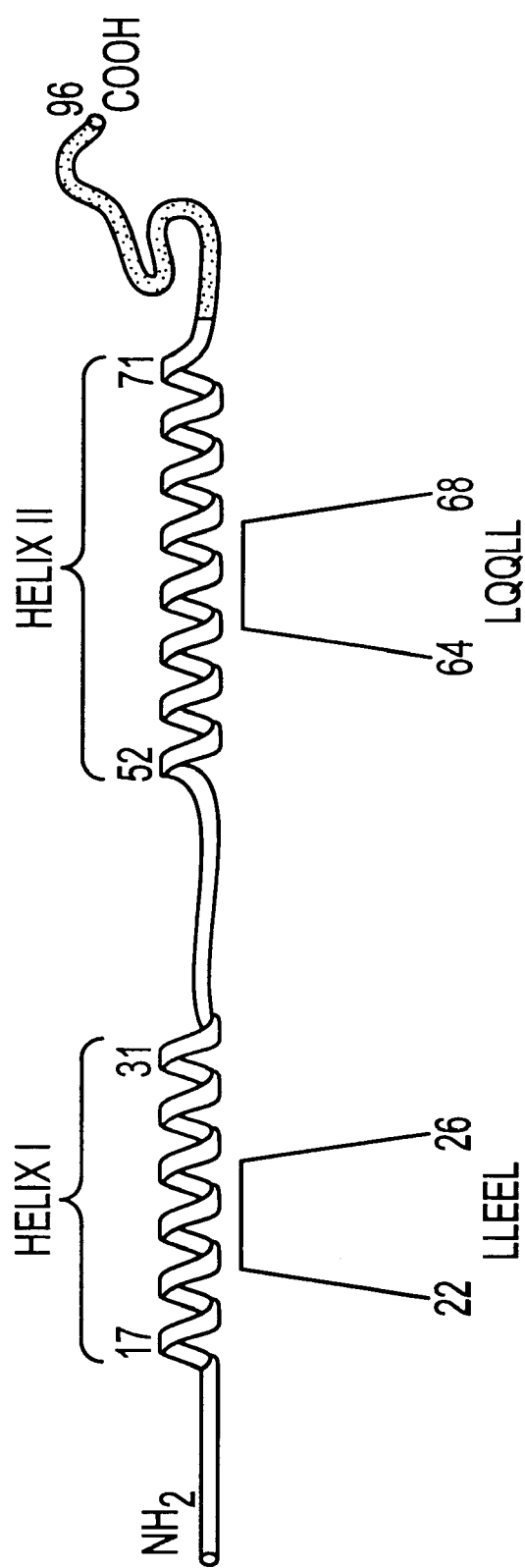
FIG. 20. Schematic diagram showing proposed secondary structure of HIV-1 Vpr

In addition, sVpr differs from other transducing proteins in that urea denaturation does not enhance its transduction properties (FIG. 11). Taken together, these results suggest that Vpr may be optimized for its transducing properties in its native state, further underscoring its potential importance in HIV biology.

Figure 24:
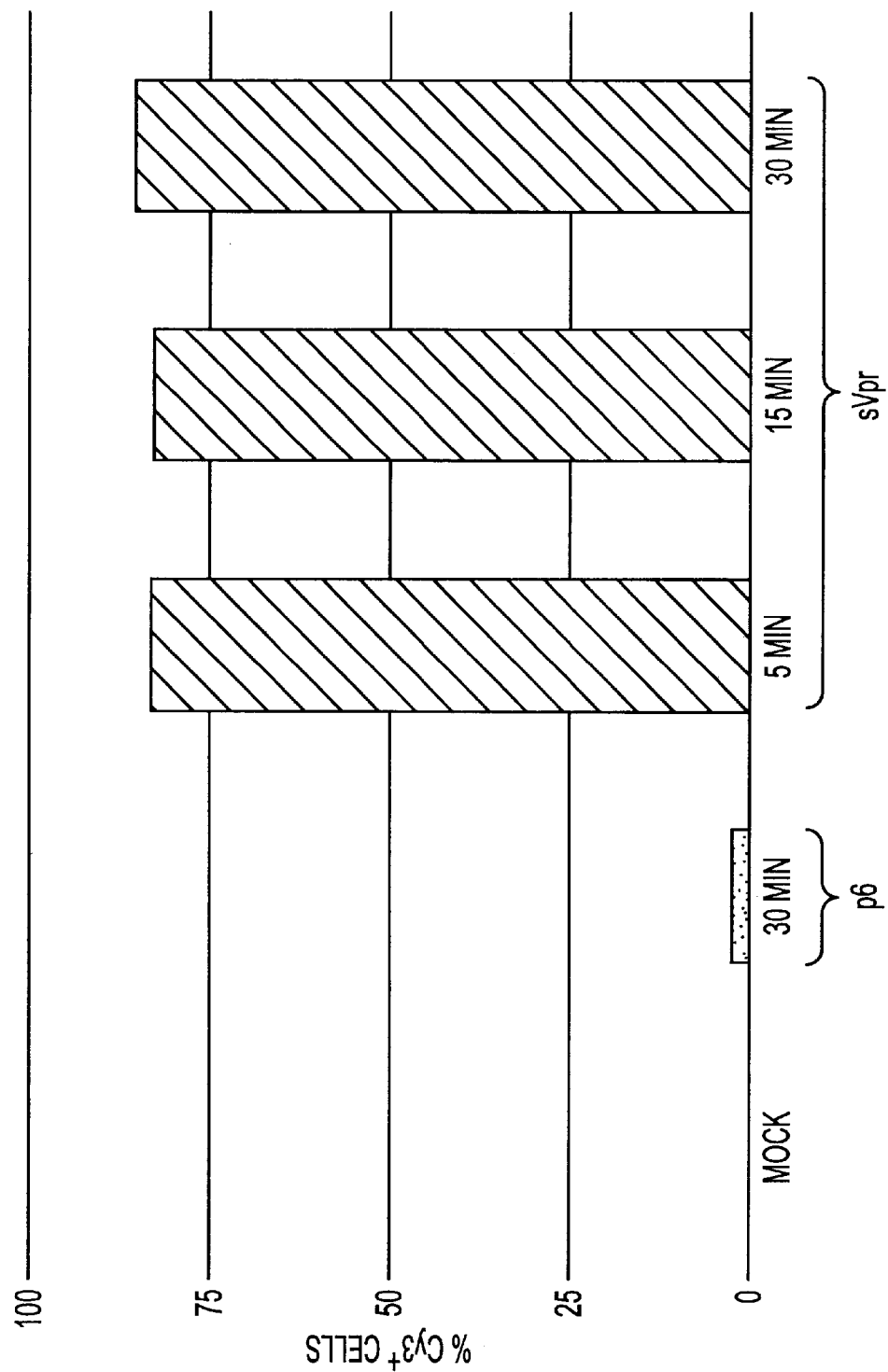
FIG. 24. sVpr uptake by Jurkat T cells is rapid. Percent Cy3-positive cells is plotted for mock, p$^6$ controls and sVpr at 5, 15 and 30 in$^{-1}$. Uptake is observed in more than $^{75}$% of cells at 5 min.
Figure 25:
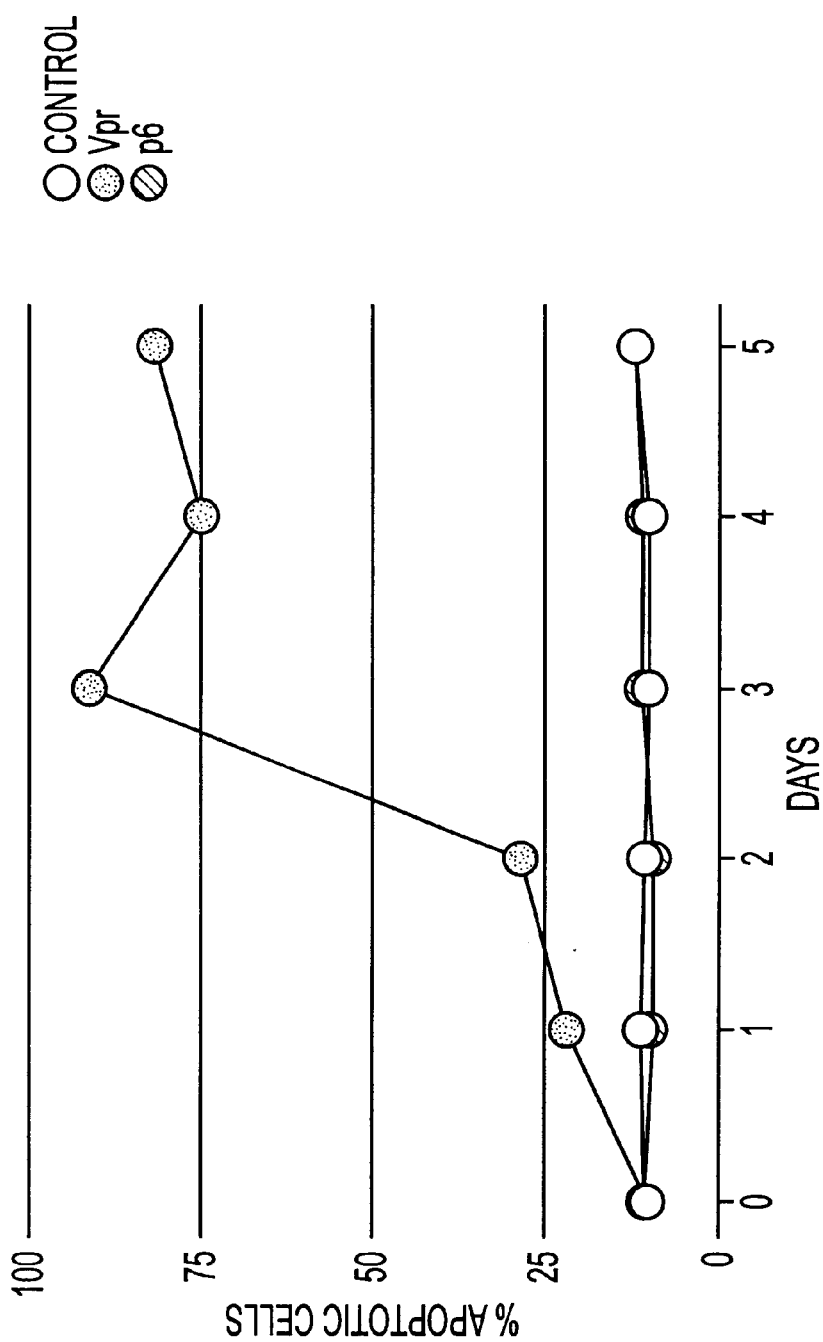
FIG. 25. sVpr induces apoptosis in Jurkat T cells. Percent apoptotic cells is plotted as a function of days after control, Vpr and p$^6$ treatment. By 3 days, approximately 90% of cells treated with sVpr are apoptotic.
Figure 26:
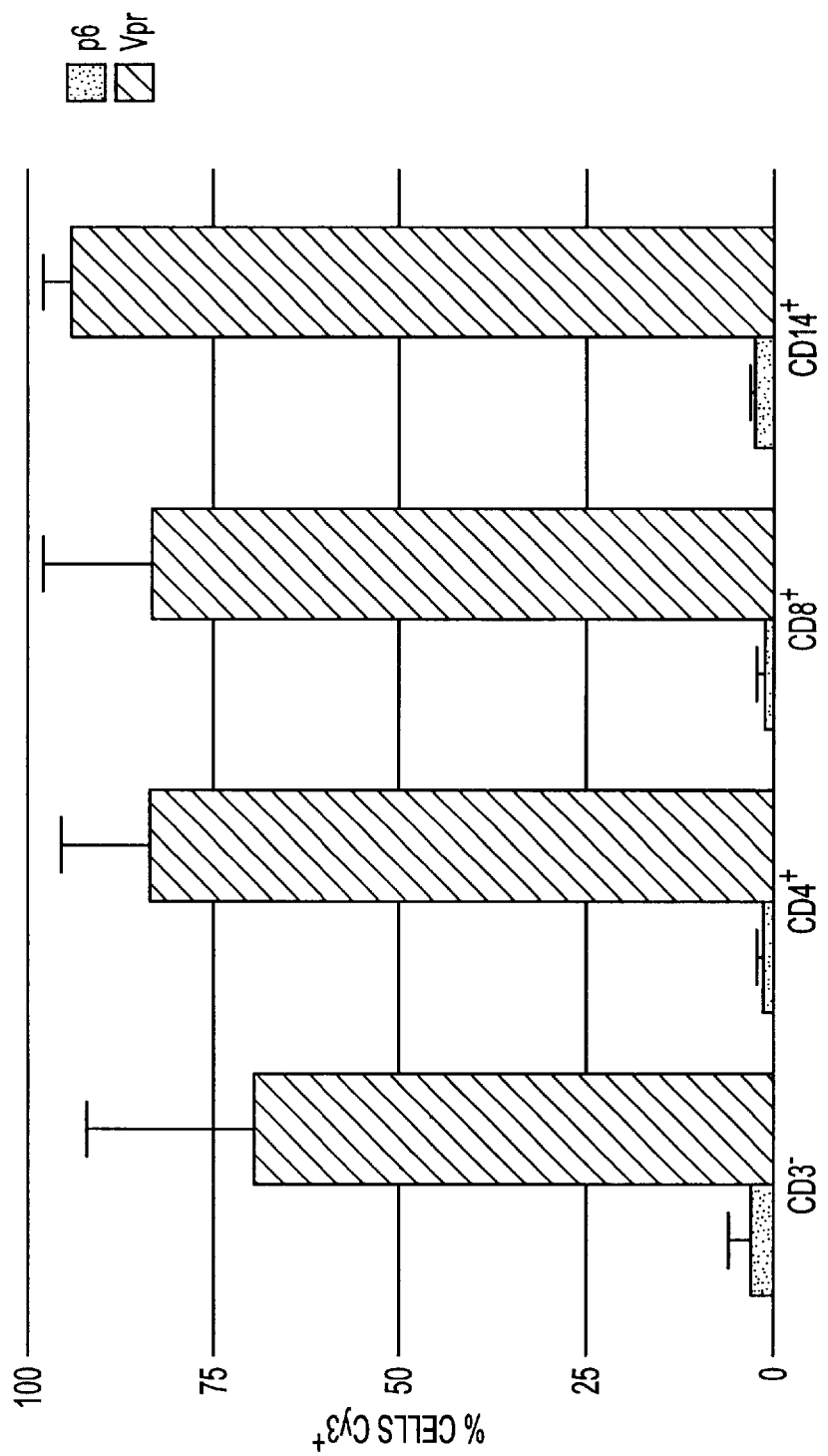
FIG. 26. sVpr transduces multiple cell types. Percent Cy3-positive cells is plotted for CD3–, CD4+, CD8+, and CD14+ cells treated with p6 (control) or sVpr.
Figure 27:
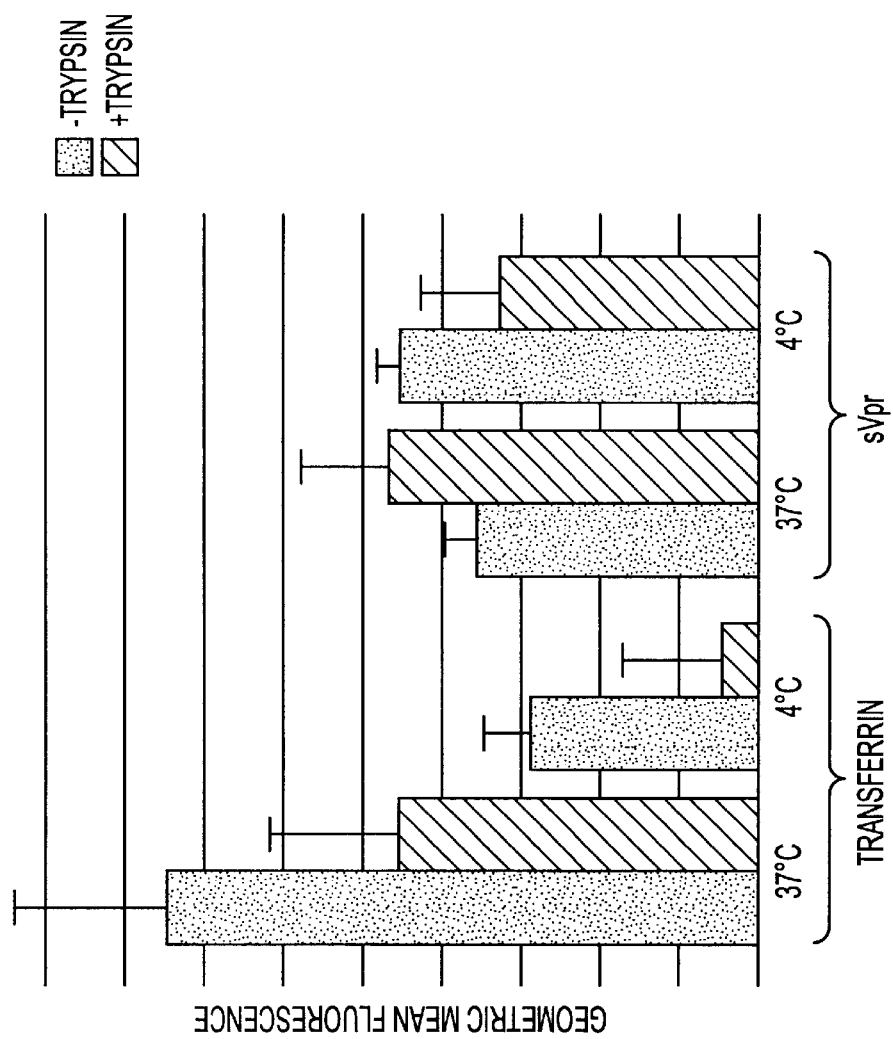
FIG. 27. sVpr enters cells at 4° C. Geometric mean fluorescence is plotted for cells treated with transferrin or sVpr in the presence or absence of trypsin at 37° C. or 4° C.

Moreover, sVpr rapidly and strongly transduces freshly isolated primary human cells at nanomolar concentrations (FIG. 24). Analysis of freshly isolated mixed cell populations reveals that CD4+, CD8+, and CD3− lymphocytes as well as CD14+ monocytes are equivalently transduced by sVpr (FIGS. 16A–H; FIG. 26). Transduced human Jurkat T cells accumulate in the G2 phase of the cell-cycle (FIGS. 15A–E). Additionally, full-length sVpr was found to induce apoptosis in cultured T-cells (FIG. 25). Further, transduced sVpr concentrates in the nuclei of monocyte-derived macrophages and significantly increases the replication of HIV viruses lacking Vpr in these cells (FIGS. 10A–B and 23A–D).

Figure 22:
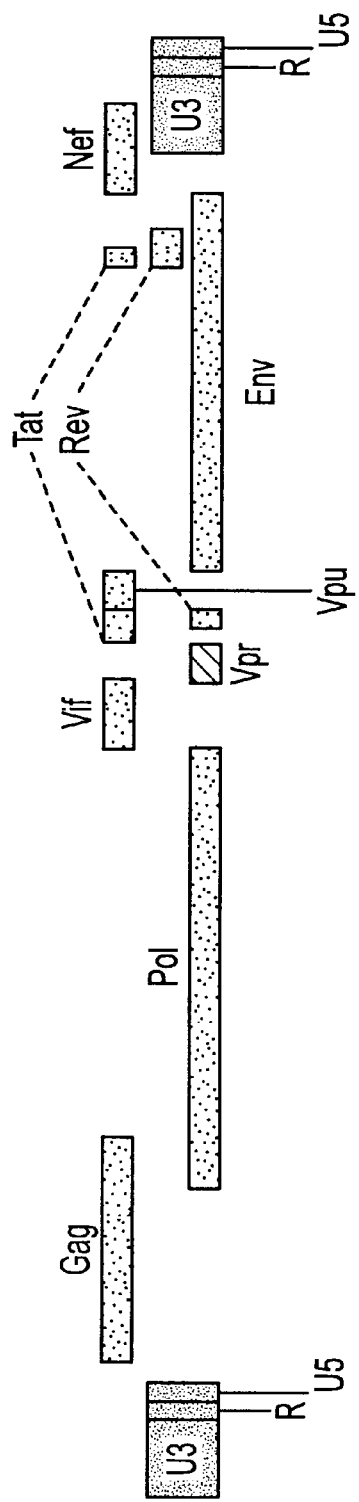
FIG. 22. Schematic diagram of HIV-1 showing position of Vpr relative to other elements of HIV-1.
Figure 23B:
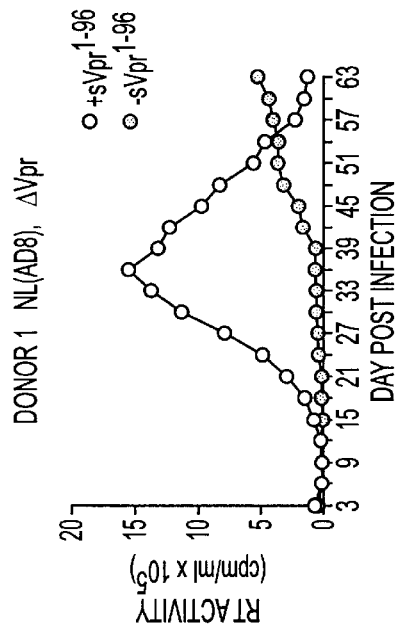
FIGS. 23A–D. Addition of sVpr to the extracellular medium enhances HIV-1 ΔVpr replication in macrophages. RT activity as a function of days post infection is plotted for wild type (A) and ΔVpr (B–D) with and without addition of sVpr$_{1-96}$.
Figure 23D:
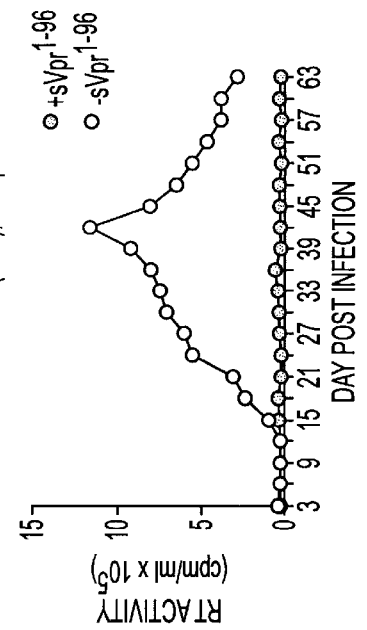
Figure 23A:
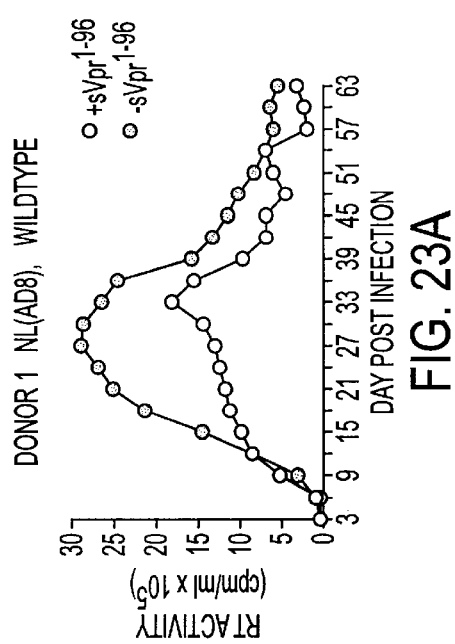
Figure 23C:
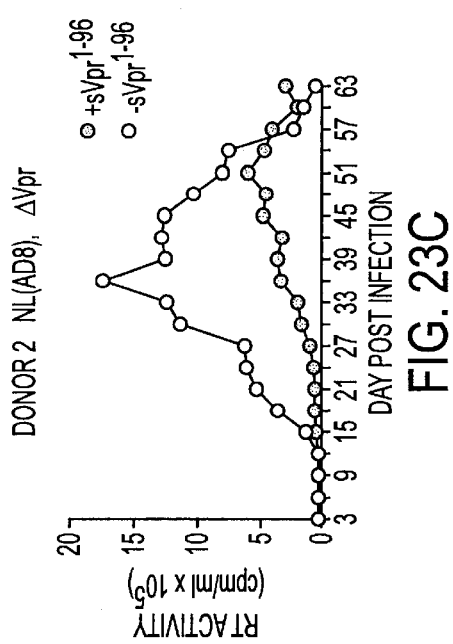

These studies demonstrate that HIV-1 Vpr is optimized for protein transduction, including apparent receptor independence and rapid uptake under conditions of limited energy. Such protein transducing properties may allow HIV to extend its effects to host cells not directly infected with the virus. FIG. 22 is a schematic representation of the HIV-1 genome, showing the relative position of Vpr. Vpr is a small protein of 96 amino acids, 14 kD, that likely multimerizes. Vpr is contained in the HIV-1 particle, binds $p6^{Gag}$, and is incorporated into virion at high stoichiometry through interaction with $p6^{Gag}$. Its structure has been surmised by CD and NMR, and found to include two leucine-rich helices and a C-terminal arginine-rich domain. It has a highly conserved ORF in vivo, and contains at least two NLS signals: 1–71 (β-Gal;BSA) and 73–96 (β-Gal). Vpr contains at least two nuclear localization signals that likely contribute to nuclear targeting of the viral preintegration complex.

REFERENCES

1. Lang, S. M., Weeger, M., Stahl-Hennig, C., Coulibaly, C., Hunsmann, G., Müller, J., Müller-Hermelink, H., Fuchs, D., Wachter, H., Daniel, M. M., Desrosiers, R. C., and Fleckenstein, B. (1993) *J. Virol.*, 67, 902–912
2. Gibbs, J. S., Lackner, A. A., Lang, S. M., Simon, M. A., Sehgal, P. K., Daniel, M. D. and Desrosiers,R.C. (1995)*J. Virol,* 69, 2378–2383
3. Heinzinger, N. K., Bulkrinsky, M. I., Haggerty, S. A., Ragland, A. M., Kewalramani, V., Lee, M. -A., Gendelman, H. E., Ratner, L., Stevenson, M. and Emerman, M. (1994) *Proc. Natl. Acad. Sci. USA,* 91, 7311–7315
4. Jenkins, Y., McEntee, M., Weis, K. and Greene, W. C. (1998) *J. Cell. Biol.,* 143, 875–885
5. Vodicka, M. A., Koepp, D. M., Silver, P. A. and Emermnan, M. (1998) *Genes Dev.,* 12, 175–185
6. Popov, S., Rexach, M., Zybarth, G., Reiling, N., Lee, M. A., Ratner, L., Lane, C. M., Moore, M. S., Blobel, G. and Bukrinsky, M. (1998) *EMBO J.,* 17, 909–917
7. Popov, S., Rexach, M., Ratner, L., Blobel, G., and Bukrinsky, M. (1998) *J. Biol. Chem.* 273, 13347–13352
8. Bukrinsky, M. and Adzhubei, A. (1999) *Rev. Med. Virol,* 9, 3949
9. Emernan, M. (1996) *Curr. Biol.,* 6,1096–1103
10. Levy, D. N., Fernandes, L. S., Williams, W. V. and Weiner, D. B. (1993) *Cell* 72, 541–550
11. Rogel, M. E., Wu, L. I., and Emerman, M. (1995)*J. Virol* 69, 882–8
12. Goh, W. C., Rogel, M. E., Kinsey, C. M., Michael, S. F., Fultz, P. N., Nowak, M. A., Hahn, B. H. and Emennan, M (1998) *Nat. Med.,* 4, 65–71
13. Poon, B., Grovit-Ferbas, K., Stewart, S. A. and Chen, I. S. Y. (1998) *Science,* 281, 266–269
14. Hrimech, M., Yao, X. J., Bachand, F., Rougeau, N., Cohen, E. A. (1999) *J. Virol.* 73, 4101–4109
15. Piller, S. C., Ewart, G. D., Premkumar, A., Cox, G. B. and Gage, P. W. (1996) *Proc. Natl. Acad. Sci. USA,* 93, 111–115
16. Cohen, E. A., Terwilliger, E. F., Jalinoos, Y., Proulx, J., Sodroski, J. G., and Haseltine, W. A. (1990) *JAIDS* 3,11–18
17. Stark, L. A. and Hay, R. T. (1998) *J. Virol.* 72, 3037–3044
18. Felzien, L. K., Woffendin, C., Hottiger, M. O., Subbramanian, R. A., Cohen, E. A., Nabel, G. J. (1998) *Proc. Natl. Acad. Sci. USA,* 95, 5281–5286
19. Wang, L., Mukherjee, S., Jia, F., Narayan, O. and Zhao, L.-J. (1995) *J. Biol. Chem.,* 270, 25564–25569
20. Kino, T., Gragerov, A., Kopp, J. B., Stauber, R. H., Pavlakis, G. N., Chrousos, G. P. (1999) *J. Exp. Med.,* 1, 51–61
21. Stewart, S. A., Poon, B., Jowett, J. B. and Chen, I. S. (1997) *J. Virol,* 71, 5579–5592
22. Ayyavoo, V. Mahboubi, A., Mahalingam, S., Ramalingam, R., Kudchodkar, S., Williams, W. V., Green, D. R. and Weiner, D. B. (1997) *Nat. Med.,* 3, 1117–1123
23. Levy, D. N., Refaeli, Y., MacGregor, R. R. and Weiner, D. B. (1994) *Proc. NatlAcad. Sci. USA,* 91, 10873–10877
24. Levy, D. N., Refaeli, Y., and Weiner, D. B. (1995) *J. Virol,* 69, 1243–1252
25. Macreadie, I. G., Castelli, L. A., Hewish, D. R., Kirkpatrick, A., Ward, A. C. and Azad, A. A. (1995) *Proc. Natl Acad. Sci. USA,* 91, 27770–27774
26. Macreadie, I. G., Arunagiri, C. K., Hewish, D. R., White, J. F., and Azad, A. A. (1996) *Mol. Microbiol.* 19, 1185–1192
27. Cornille, F.,Wecker, K., Loffet, A., Genet, R. and Roques, B (1999) *J. Peptide Res.,* 54, 427–435
28. Zhao, L. J., Wang, L., Mukherjee, S. and Narayan, O. (1994) *J.Biol. Chem.,* 269, 32131–32137
29. Selig, L., Pages, J. C., Tanchou, V., Preveral, S., Berlioz-Torrent, C., Liu, L. X., Erdtmann, L., Darlix, J., Benarous, R. and Benichou, S. (1999) *J. Virol.* 73, 592–600
30. Bachand, F., Yao, X. J., Hrimech, M., Rougeau, N. and Cohen, E. A. (1999) *J. Bio. Chem.,* 274, 9083–9091
31. Kondo, E., Maimano, F., Cohen, E. A. and Göttlinger, H. G. (1995) *J. Virol.,* 9, 2759–2764
32. Schüler, W., Wecker, K., de Rocquigny, H., Baudat, Y., Sire, J. and Roques, B. P. (1999) *J. Mol Biol,* 285, 2105–2117
33. Luo, Z., Butcher, D. J., Murali, R., Srinivasan, A. and Huang, Z. (1998) *Biochem. Biophys. Res. Commun.,* 244, 732–736
34. Yao, S., Azad, A. A., Macreadie, I. G. and Norton, R. S. (1998) *Protein Peptide Lett.,* 5, 127–134
35. Wecker, K. and Roques, B. P. (1999) *Eur. J. Biochem.,* 266, 359–369
36. Lundgren, S., Carling, T., Hjalm, G.,Juhlin, C., Rastad,J., Pihlgren, U., Rask, L., Aketstrom, G. and Hellman, P. (1997) *J. Histochem. Cytochem.,* 45, 383–392
37. Wray, V., Federau, T., Henklein, P., Klabunde, S., Kunert, O., Schombutg, D. and Schubert, U. (1995) *Int. J. Pept. Protein Res.,* 45, 35–43
38. Gras-Masse, H., Ameisen, J. C., Boutillon, C., Gesquiere, J. C., Vian, S., Neyrinck, J. L., Drobecq, H., Capron, A. and Tartar, A. (1990) *Int. J. Pet. Protein. Res.,* 36, 219–226
39. De Rocquigny, H., Petitjean, P., Tanchou, V., Deciimo, D., Drouot, L., Delaunay, T., Darlix, J. -L. and Roques, B. P. (1997) *J. Biol. Chem.,* 272, 30753–30759
40. Roques, B. P., Morellet, N., de Rocquigny, H., Demene, H., Schüler, W., Jullian, N. (1997) *Biochimie,* 79, 673–680
41. Wang, L., Mukherjee, S., Narayan, O., Zhao, L. -J. (1996) *Gene,* 178, 7–13
42. Nie, Z., Bergeron, D., Subbramanian, R. A., Yao, X. J., Checroune, F., Rougeau, N., Cohen, E. A. (1998)*J. Virol.,* 72, 4104–4115
43. Zhang, S., Pointer, D., Singer, G., Feng, Y., Park, K. and Zhao, L. J. (1998) *Gene,* 212, 157–166
44. Green, M., Loewenstein, P. M. (1988) *Cell,* 55, 1179–1188
45. Frankel, A. D. and Pabo, C. O. (1988) *Cell,* 55,1189–1193
46. Schwarze, S. R., Ho, A., Vocero-Akbani, A. and Dowdy, S. F. (1999) *Science,* 285, 1569–1572
47. Nagahara, H., Vocero-Akbani, A. M., Snyder, E. L., Ho, A., Latham, D. G., Lissy, N. A., Becker-Hapak, M., Ezhevsky, S. A. and Dowdy, S. F. (1998) *Nat. Med.,* 12, 1449–1452
48. Carpino, L. A. (1993)*Am. Chem. Soc.,* 115, 4397–4398
49. Adachi, A., Gentleman, H. E., König, S., Folks, T., Willey, R., Rabson, A. and Martin, M. A. (1986)*J. Virol.,* 59, 284–291
50. Moestrup, S. K., Birn, H., Fischer, P. B., Petersen, C. M., Verroust, P. J., Sim, R. B., Christensen, E. I. and Nexo, E. (1996) *Proc. Natl. Acad. Sci. USA,* 93, 8612–8617

Those skilled in the art will appreciate that the conceptions and specific embodiments disclosed in the foregoing description may be readily utilized as a basis for modifying or designing other embodiments for carrying out the same purposes of the present invention.

What is claimed is:

1. A method for delivering a molecule into a cell comprising contacting the extracellular compartment of the cell with a conjugate comprising a Vpr polypeptide conjugated to the molecule, wherein the conjugate crosses the plasma membrane of the cell.

2. The method of claim 1, wherein the molecule is delivered to the nucleus of the cell.

3. The method of claim 1, wherein the Vpr comprises synthetic Vpr.

4. The method of claim 3, wherein the synthetic Vpr is stable in aqueous solution.

5. The method of claim 1, wherein the molecule comprises a polypeptide.

6. The method of claim 1, wherein the molecule comprises a polynucleotide.

7. The method of claim 6, wherein the polynucleotide comprises DNA or RNA.

8. The method of claim 1, wherein the molecule comprises a toxin.

9. The method of claim 1, wherein the cell is a cancer cell.

10. The method of claim 1, wherein the cell is infected with a pathogen.

11. The method of claim 10, the pathogen is a virus, a bacterium or a parasite.

12. The method of claim 11, wherein the virus is a lentivirus or a retrovirus.

13. The method of claim 12, wherein the lentivirus is HIV.

14. The method of claim 1, wherein the cell is genetically modified to express a transgene.

* * * * *

UNITED STATES PATENT AND TRADEMARK OFFICE
CERTIFICATE OF CORRECTION

PATENT NO.    : 6,664,040 B2
DATED         : December 16, 2003
INVENTOR(S)   : Michael P. Sherman et al.

It is certified that error appears in the above-identified patent and that said Letters Patent is hereby corrected as shown below:

Title page,
Item [73], Inventors, after "Berlin", "(GB)" should read -- (DE) --.

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,664,040 B2
DATED         : December 16, 2003
INVENTOR(S)   : Michael P. Sherman et al.

It is certified that error appears in the above-identified patent and that said Letters Patent is hereby corrected as shown below:

<u>Title page,</u>
Item [75], Inventors, after "Berlin", "(GB)" should read -- (DE) --.

This certificate supersedes Certificate of Correction issued September 28, 2004.

Signed and Sealed this

Thirtieth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,664,040 B2
DATED : December 16, 2003
INVENTOR(S) : Michael P. Sherman et al.

It is certified that error appears in the above-identified patent and that said Letters Patent is hereby corrected as shown below:

Title page,
Item [73], Assignee, after "Oakland, CA (US)", insert -- The J. David Gladstone Institutes, San Francisco, CA (US) --.

Signed and Sealed this

Twenty-second Day of November, 2005

JON W. DUDAS
*Director of the United States Patent and Trademark Office*